US010458831B2

(12) United States Patent
Cunningham et al.

(10) Patent No.: US 10,458,831 B2
(45) Date of Patent: Oct. 29, 2019

(54) SYSTEM AND METHOD FOR ACOUSTIC CONTAINER VOLUME CALIBRATION

(71) Applicant: Saudi Arabian Oil Company, Dhahran (SA)

(72) Inventors: Vincent Cunningham, Ferbane (IE); Ali Outa, Thuwal (SA); Ihsan A-Taie, Dhahran (SA); Ayman Amer, Thuwal (SA)

(73) Assignee: SAUDI ARABIAN OIL COMPANY, Dhahran (SA)

(*) Notice: Subject to any disclaimer, the term of this patent is extended or adjusted under 35 U.S.C. 154(b) by 69 days.

(21) Appl. No.: 15/641,516

(22) Filed: Jul. 5, 2017

(65) Prior Publication Data
US 2019/0011304 A1    Jan. 10, 2019

(51) Int. Cl.
*G01F 17/00* (2006.01)
*G01F 25/00* (2006.01)
(Continued)

(52) U.S. Cl.
CPC .......... *G01F 17/00* (2013.01); *G01F 23/2962* (2013.01); *G01F 25/0084* (2013.01);
(Continued)

(58) Field of Classification Search
USPC .......................................................... 73/149
See application file for complete search history.

(56) References Cited
U.S. PATENT DOCUMENTS 3,930,404 A    1/1976 Ryden, Jr.
5,119,676 A    6/1992 Bower et al.
(Continued)

FOREIGN PATENT DOCUMENTS

DE    3844340 A1    7/1990
DE    102004028547 A1    2/2006
(Continued)

OTHER PUBLICATIONS

International Search Report and Written Opinion in corresponding International Patent Application No. PCT/US2018/035786, dated Sep. 27, 2018. 16 pages.
(Continued)

*Primary Examiner* — Clayton E. LaBalle
*Assistant Examiner* — Warren K Fenwick
(74) *Attorney, Agent, or Firm* — Leason Ellis LLP

(57) ABSTRACT

A system and method is disclosed for calibrating the volume of storage containers using ultrasonic inspection techniques. The exemplary ultrasonic calibration system comprises a plurality of acoustic devices controllably deployed in respective positions on the outside surface of the container. The acoustic devices include a transducer for sending acoustic signals across the internal volume of the container and sensors configured to detect the acoustic signals. The acoustic devices are in communication with a diagnostic computing device that controls the positioning and the operation of the acoustic devices and is further configured to determine the time time-of-flight of acoustic signals that travel between the various acoustic devices. Moreover, according to the specific arrangement of acoustic devices and the measured acoustic signal information, the control computer is configured to calculate the dimensions of the container and its internal volume.

13 Claims, 11 Drawing Sheets

(51) Int. Cl.
*G01N 29/024* (2006.01)
*G01N 29/22* (2006.01)
*G01N 29/265* (2006.01)
*G01F 23/296* (2006.01)

(52) U.S. Cl.
CPC ......... *G01N 29/024* (2013.01); *G01N 29/225* (2013.01); *G01N 29/265* (2013.01); *G01N 2291/02854* (2013.01); *G01N 2291/101* (2013.01); *G01N 2291/102* (2013.01)

(56) References Cited

U.S. PATENT DOCUMENTS

| | | | |
|---|---|---|---|
| 5,251,487 | A | 10/1993 | Marshall |
| 5,487,300 | A | 1/1996 | Brackett et al. |
| 5,563,346 | A | 10/1996 | Bartelt et al. |
| 6,104,970 | A | 8/2000 | Schmidt, Jr. et al. |
| 6,259,516 | B1 | 7/2001 | Carter et al. |
| 6,573,732 | B1* | 6/2003 | Reimer ............... B60K 15/077 324/644 |
| 6,813,950 | B2 | 11/2004 | Glascock et al. |
| 6,922,234 | B2 | 7/2005 | Hoffman et al. |
| 6,925,870 | B2* | 8/2005 | Pappas ............... G01F 23/2962 73/290 V |
| 7,246,552 | B2 | 7/2007 | Diaz et al. |
| 7,373,839 | B2* | 5/2008 | Wiest .................. G01F 1/662 73/861.23 |
| 8,593,908 | B2 | 11/2013 | Ferreira et al. |
| 8,848,171 | B2 | 9/2014 | Stutz et al. |
| 2006/0123922 | A1 | 6/2006 | Froehlich et al. |
| 2012/0226159 | A1 | 9/2012 | Sinclair et al. |
| 2012/0281096 | A1* | 11/2012 | Gellaboina ............ G01F 23/292 348/163 |
| 2013/0035894 | A1 | 2/2013 | Greiner et al. |
| 2016/0041024 | A1* | 2/2016 | Reimer ............... G01F 23/2962 73/290 V |
| 2016/0320219 | A1 | 11/2016 | Hellevang et al. |
| 2016/0320226 | A1* | 11/2016 | Schaefer ............. G01F 23/2962 |
| 2017/0010146 | A1* | 1/2017 | Kassubek ............ G01N 29/222 |
| 2017/0102362 | A1* | 4/2017 | Sackmann ........... B01L 3/0268 |
| 2018/0306628 | A1* | 10/2018 | Parrott ................... G01F 17/00 |

FOREIGN PATENT DOCUMENTS

| | | |
|---|---|---|
| EP | 2520909 A1 | 11/2012 |
| EP | 3115753 A1 | 1/2017 |
| WO | 1984001233 A1 | 3/1984 |

OTHER PUBLICATIONS

American Petroleum Institute Manual of Petroleum Measurement Standards. Chapter 2, Tank Calibration, Section 2A, Measurement and Calibration of Upright Cylindrical Tanks by the Manual Tank Strapping Method. Feb. 1995. Reaffirmed Aug. 2017. 68 pages.

American Petroleum Institute Manual of Petroleum Measurement Standards. Chapter 2, Tank Calibration, Section 2B, Calibration of Upright Cylindrical Tanks Using the Optical Reference Line Method. Mar. 1989. Reaffirmed Jan. 2013. 14 pages.

American Petroleum Institute Manual of Petroleum Measurement Standards. Chapter 2, Tank Calibration, Section 2C, Calibration of Upright Cylindrical Tanks Using the Optical-Triangulation Method. Jan. 2002. Reaffirmed Apr. 2013 27 pages.

American Petroleum Institute Manual of Petroleum Measurement Standards. Chapter 2, Tank Calibration, Section 2D, Calibration of Upright Cylindrical Tanks Using the Internal Electro-optical Distance-ranging Method. Aug. 2003. Reaffirmed Mar. 2014. 19 pages.

Satyanarayan, L. et al. "Simulation of ultrasonic phased array technique for imaging and sizing of defects using longitudinal waves." International Journal of Pressure Vessels and Piping, 2007, pp. 716-729.

\* cited by examiner

SYSTEM AND METHOD FOR ACOUSTIC CONTAINER VOLUME CALIBRATION

FIELD OF THE INVENTION

The present invention relates to systems and methods for non-destructive testing of structures, in particular to systems and methods for acoustic measurement of the geometry of containers in a non-destructive manner.

BACKGROUND

In the oil and gas industry the storage tanks for crude and refined products play a key part in the supply chain of hydrocarbons. Knowing the exact volume of these storage units plays a critical role when transferring products to and/or from the tanks. As a result of variations in external and internal conditions (i.e. temperature) and aging and also as a result of the weight of the liquid product (i.e. hydrostatic pressure), the tank volume can vary by as much as +/−0.2%. Considering a 250,000 barrel storage tank, this variation would result in a volume of +/−500 barrels in volume change.

As a result of the high value of petroleum hydrocarbons, there is a mandatory requirement for calibration of storage tanks. Tanks used for custody transfer must be calibrated such that the transferred volume is very accurately known (e.g., Less than 0.1% error). The most commonly used techniques to perform this are; manual strapping (API MPMS 2.2A), optical techniques (Optical Reference Line Method ORLM-API Chapter 2.2B, Optical Triangulation Method (OTM)—API Chapter 2.2C, Electro-Optical Distance Ranging Method (EODR)—API Chapter 2.2D) and liquid calibrations (API Standard 2555). However, these measurements have been found to produce errors and are considered non-effective. In some cases, the foregoing testing techniques require tank downtime (e.g., emptying of the tank or otherwise halting the tank operation temporarily), which accumulates additional costs to the losses incurred. Moreover, many of the foregoing testing techniques are invasive in that they require accessing the internal volume of the tank and also can be destructive.

In the oil and gas industry, ultrasonic probes have been used to determine the health and structural integrity of pipelines and vessels at localized points. Known systems for measuring wall thickness using ultrasound are based on the concept of using the time-of-flight (TOF) for sound to travel between the outer and inner surfaces of the wall to determine distance traveled. In such implementations, the TOF analysis of the ultrasonic signals return journey through the metallic medium (i.e. pipe or vessel) is used to determine the thickness of the wall and, thus, degradation as a result of corrosion. Similarly, there has been work on sending acoustic waves along the length of pipes to determine if there are cracks or other anomalies that would cause unexpected reflections. However, such systems are reliant on known or assumed pipe dimensions and are not configured to determine the geometric profile of the pipe. Rather, the geometric measurement of the container is assumed or determined using the known alternative methods mentioned above.

In the case of tank inspection, the aforementioned methods require high levels of calibration and also require a couple of days' worth of work (e.g., including the erection and use of high scaffolding to deploy the measuring systems and conduct the measurements). Therefore, calibration/measurement of the tanks is done infrequently, leading to erroneous tank volumes and lost sales revenue.

The existing methods for tank calibration present significant drawbacks. For instance, using the current standards, it can take 1-2 days of work to perform the calibration. As a result, calibration of storage tanks is performed infrequently thus leading to inaccurate measurements of the actual volume stored within the tank or transferred to and from the tank, which can be costly. For example, a traditional timeframe between calibrations can be between five and fifteen years.

What is needed are systems and methods for calibrating the volume of storage tanks that addresses the limitations associated with the efficiency of performing calibration using existing systems. More specifically, what is needed are systems and methods for accurately performing tank calibration that can be deployed and operated in a relatively quick, low-cost, and non-invasive manner. What is also needed is a system that can be deployed quickly and on-demand and thus facilitates detection of changes in tank volume on a more frequent basis (e.g., on a daily basis or even per-fill basis).

It is with respect to these and other considerations that the disclosure made herein is presented.

SUMMARY

According to an aspect of the present invention, there is provided a method for measuring a container containing a medium therein using a plurality of acoustic devices. The method includes the step of deploying the plurality of acoustic devices into respective positions on an exterior surface of a circumferential wall of the container. In particular, the acoustic devices include an ultrasonic transducer and an ultrasonic sensor. The transducer is acoustically coupled to the surface and is configured to transmit one or more ultrasonic signals through the wall of the container and across the interior volume of the container. In addition, the sensor is acoustically coupled to the surface and configured to detect the one or more ultrasonic signals. The method also includes the steps of transmitting one or more ultrasonic signals using the transducer at a respective impulse time and detecting the one or more signals, using the sensor, and recording a respective detection time. The method also includes the step of calculating, by a computing device that is in electronic communication with the transducer and the sensor, respective times of flight (TOFs) for the one or more signals based on the respective impulse times and respective detection times. More specifically, each respective TOF is an elapsed time for a signal to travel through the interior volume between the transducer and the sensor along a respective flightpath. The method also includes a step of aligning one or more of the acoustic devices based on the calculated TOFs. In particular, the devices are aligned in one or more of a circumferential direction and a longitudinal direction relative to the circumferential wall of the container. According to the method, the steps of transmitting, detecting and calculating are repeated. In addition, the method includes the step of calculating, with the computing device, a distance between the aligned transducer and sensor based on the re-calculated TOF and a speed of sound through the medium. Lastly, the method includes the step of determining, with the computing device, the volume of the storage container based on the calculated distances.

According to a further aspect of the present invention, there is provided a system for measuring a volume of a storage container. The system comprises a plurality of acoustic devices that are configured to be acoustically coupled to an exterior surface of a circumferential wall of the container at respective positions, the acoustic devices including. In particular, the acoustic devices include an ultrasonic transducer configured to transmit one or more ultrasonic signals across an interior volume of the container that is bounded by the wall, and an ultrasonic sensor configured to detect the one or more ultrasonic signals. The system also includes a robot configured to controllably deploy one or more of the acoustic devices on the surface. In particular, the robot includes a drive system and one or more position sensors for monitoring a position of the robot.

The system also includes a computing system that comprises a non-transitory computer readable storage medium and one or more processors in electronic communication with the plurality of acoustic devices and the computer readable storage medium. The computing system also includes one or more software modules comprising executable instructions that are stored in the storage medium and are executable by the processor. In particular, the software modules include an acoustic control module that configures the processor, using the transducer, to transmit one or more acoustic signals at respective impulse times. In addition, the acoustic control module further configures the processor, using the sensor, to detect the arrival of the one or more signals and record respective detection times. The software modules also includes an acoustic analysis module that configures the processor to calculate a respective time of flight (TOF) for the one or more acoustic signals traveling between the respective positions of the transducer and the sensor. Further the configured processor calculates a respective distance therebetween based on the respective TOF. The software modules also includes a position control module that configures the processor to, using the robot, adjust the respective position of one or more of the transducer and the sensor on the surface. In addition, for each adjusted respective position, the processor is configured to re-calculate a respective distance between the transducer and the sensor based on one or more acoustic signals traveling therebetween. The software modules also include a geometric analysis module that configures the processor to calculate a volume of the storage container based on the calculated respective distances and corresponding respective positions of the transducer and the sensor.

These and other aspects, features, and advantages can be appreciated from the accompanying description of certain embodiments of the invention and the accompanying drawing figures and claims.

DETAILED DESCRIPTION OF CERTAIN EMBODIMENTS OF THE INVENTION

Figure 1:
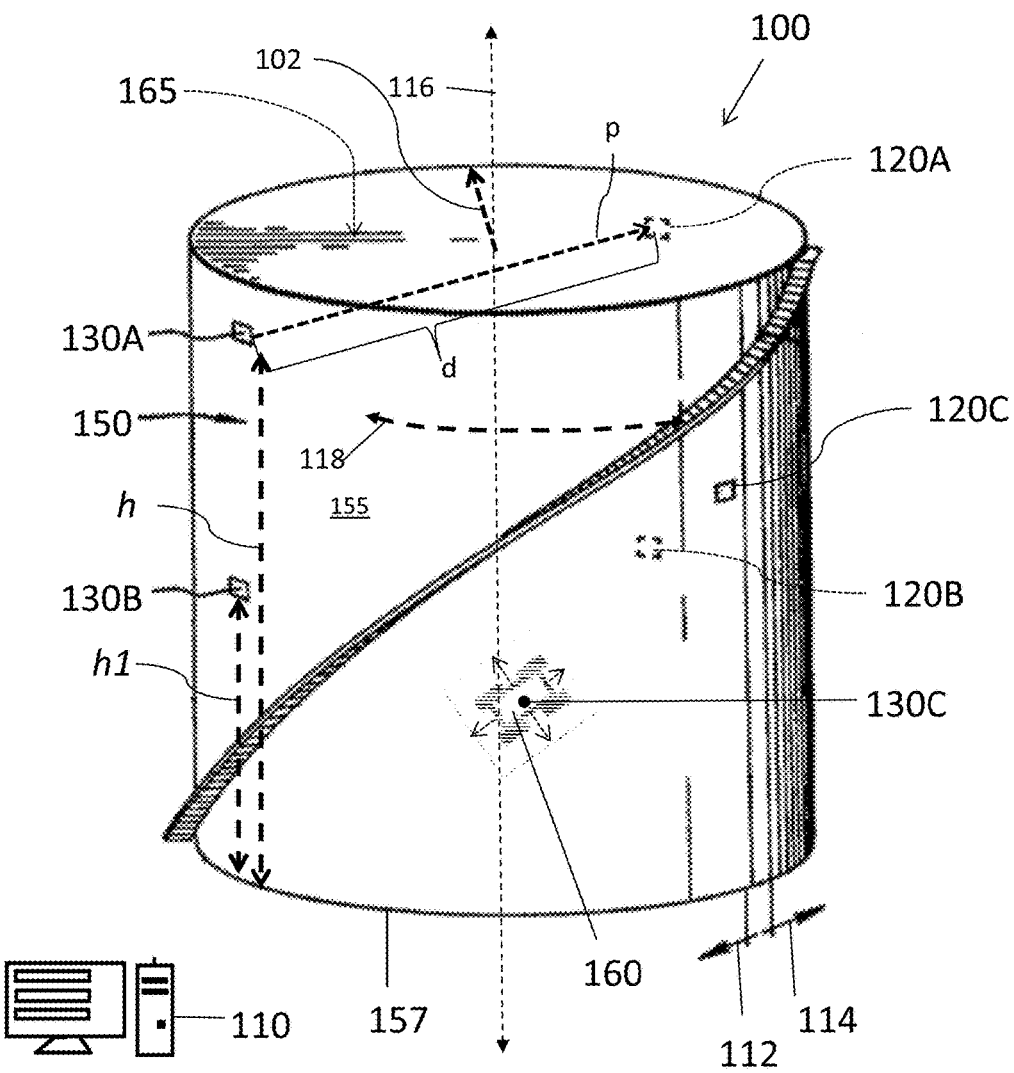
FIG. 1 is a high-level diagram illustrating an exemplary configuration of a system for ultrasonic calibration of the volume of storage containers according to an embodiment of the invention.

By way of overview and introduction, a system and method is disclosed for calibrating the volume of storage containers. More specifically, the systems and methods disclosed herein are directed to measuring and determining the dimensions of large petroleum storage tanks so as to calculate the volume of such tanks using ultrasonic inspection techniques. Preferably, the systems are configured to perform the calibration from the exterior of the container on-demand during the use of the containers in the field. "Calibrating," i.e., knowing the exact volume of the storage containers, plays a critical role when transferring products to and/or from the tanks. Routine calibration is necessary due to variations in external and internal conditions (i.e. temperature), aging of the tank, and also as a result of the weight of the liquid product (i.e. hydrostatic pressure). For example, a container's volume can vary by as much as +/−0.2%, considering a 250,000 barrel storage this would result in a volume of +/−500 barrels in volume change.

Ultrasonic testing is a non-destructive and non-invasive testing technique based on analyzing the propagation of ultrasonic waves in the material being tested (e.g., the wall of the container). In the embodiments described herein, the ultrasonic measuring techniques are performed to measure the volume of large storage containers that are typically generally cylindrical in shape and are typically made of steel or other metals and alloys. However, the disclosed techniques and systems can also be applied to calibrate the volume of structures made of other materials such as concrete, composites, natural materials (e.g., wood) or combinations of the foregoing. In addition, the systems and techniques disclosed herein can also be applied to measure the volume of containers having different sizes and shapes as well. For instance, the exemplary embodiments can be used to measure the volume of open or closed vessels, tanks and other such containers or conduits of various sizes.

In some exemplary configurations, the ultrasonic container volume calibration system comprises a plurality of acoustic devices having associated electronic hardware and/or software suitable for controlling their operation. The acoustic devices are configured to be attached to the exterior surface(s) of a storage container, for instance, by hand or using a mobile robotic platform and the like, thereby defining one or more arrays of devices. The acoustic devices are configured to take acoustic-based measurements that enable the determination of the container's volume by a diagnostic computing device that is in communication with the acoustic devices. More specifically, the acoustic devices include one or more acoustic sensors configured to receive, measure and process acoustic signals transmitted across the internal volume of the container. The acoustic devices also include at least one acoustic signal generating element (hereinafter also referred to as a "transducer") that is configured to transmit the acoustic signals through the wall of the container and across the interior volume of the container and, accordingly, through any particular medium contained therein (e.g., oil, water, air and the like).

In some basic configurations, the ultrasonic container volume calibration system includes one transducer and one sensor. The transducers and sensors can be individual acoustic devices, however, in some implementations a transducer and sensor can be integrated into a single transceiver unit configured to transmit and receive acoustic signals. In more complex configurations the system includes a plurality of acoustic devices placed on the container surface at different latitudes on the surface (e.g., different heights on the container wall, as measured in the longitudinal direction relative to the base) and/or placed at different circumferential positions (i.e., spaced apart about the circumference of the container).

The acoustic sensors and transducers are connected to and controlled using a diagnostic computing device (hereinafter referred to as the controller or control computer), which is configured to determine the time between the transmission of an acoustic signal using the transducer and the arrival of the acoustic signal, which traveled across the interior volume of the container, at a respective sensor. The travel time of an acoustic signal between devices is referred to as the "time-of-flight" or "TOF." In addition, similar TOF information for additional acoustic signals that arrive at one or more of the sensor(s) can be measured/collected as well (e.g., reflections of the first acoustic signal off the interior wall of the container, or a second acoustic signal transmitted by one or more of the transducers).

According to a salient aspect, in some implementations, the acoustic devices can be controllably positioned on the surface of the container and aligned in one or more directions. For instance, a sensor and a transducer can be longitudinally aligned such that they are at the same height on the container wall, as measured relative to the base of the container, which is assumed to be on level ground for simplicity. In addition or alternatively, two devices can be aligned on the outer surface of the container in other directions, for instance, circumferentially, such that the devices are located on directly opposite sides of the container and the acoustic signals travelling therebetween follow a path that extends across the interior diameter of the container. In addition or alternatively, in some implementations, a transceiver operating in transmit and receive mode can be positioned and aligned on the container surface such that it transmits acoustic signals that travel across the interior volume, reflect off the interior surface of the opposite side of the wall and travel back along the same path to the point of origin, where it can be received using the transducer.

Accordingly, based on the time between the transmission and detection of acoustic signals and the relative position of the acoustic devices, various dimensions of the container can be calculated by the control computer, including, for example and without limitation, diameter, circumference, volume, and height. The dimensions of the container are also calculated based on the speed of sound through the medium that is contained within the interior volume and that the acoustic signals travel through. Accordingly, an accurate understanding of the speed of sound in the particular medium that is contained within the container (e.g., oil, refined product, water, air and the like) can be important to determining the actual length of the acoustic signal's flight-path and the corresponding dimensions of the container. In addition to time-of-flight analysis, transient analysis can be performed by extracting information on the phase difference between the acoustic signals to determine changes in the time of flight.

According to another salient aspect, the disclosed system for acoustic calibration of can be configured to controllably move one or more of the acoustic sensing devices into position before and/or during the container volume calibration process, for instance using robotic carriers that deploy the one or more acoustic devices on the exterior of the container being calibrated. In such embodiments, the robotic carriers can include memory and one or more processors that are programmed to position the devices and perform acoustic distance measurements autonomously and/or controlled remotely using the control computer. In particular, the robots can controllably move the acoustic devices so as to measure the diameter of the container at different points along the height of the container and/or around the circumference of the container. For instance, one or more robotic platforms can be configured to follow a pre-determined and pre-programmed path along the surface, say, a helical path about the container's circumference starting near a top edge of the wall to the base, so as to take acoustic measurements at different heights and circumferential positions and store the temporal information from the acoustic signals and positional information of the acoustic devices for each measurement in storage at the robotic platform or control computer.

In addition, in such embodiments, alignment in a variety of different directions/dimensions can be achieved among the acoustic devices and relative to the surface of the container wall to improve calculations of volume of a container. As a result of measuring distance across the interior volume of the container from multiple positions on the side-wall of the container, a two-dimensional map or three dimensional model of the container can be created using the measured distances therebetween and principles of geometry.

An exemplary system for ultrasonic calibration of the volume of a storage container 100 is shown in FIG. 1. As shown in FIG. 1, the ultrasonic container volume calibration system 100 includes one or more acoustic devices that are arranged for measuring the volume of a metallic, cylindrical storage container 150. The container includes a circumferential side wall that bounds the interior volume 165 of the container. It can be appreciated that cylindrical containers are not necessarily exact cylinders that extend vertically. For example and without limitation, the cylinder's circumference can differ at different heights on the wall, the side-wall of the container can have a non-uniform curvature and the container can have other such variations in geometry. By way of further example, in some implementations, the cylinders can be oriented such that the central axis extends horizontally relative to the ground. Moreover, the exemplary techniques disclosed herein are similarly applicable to calibrating the volume of containers having other shapes, for instance, spherical tanks, however, it can be appreciated that such alternative container shapes can require a different set of known parameters (e.g., relative placement or distance between measurement devices) in order to calculate the container volume.

The one or more acoustic devices are configured to be deployed onto the exterior surface 155 of the side wall (e.g. by hand, robot, etc.) and acoustically coupled to the wall of the container. Accordingly, the acoustic devices are configured to transmit acoustic signals and/or receive acoustic signals traveling through the volume of the container. The one or more acoustic devices preferably include at least one acoustic sensor and at least one acoustic transducer.

As shown in FIG. 1, the acoustic devices can include one or more sensors 120A (shown on the opposite side of the container), 120B (shown on the opposite side of the container) and 120C that are arranged on the surface 155. In addition, the system 100 includes one or more transducers, for instance, transducer 130A, that is configured to generate and apply acoustic signals to the surface 155 that are suitable for detection by acoustic sensors. Additional transducers such as transducer 130B and 130C can also be used.

The term "longitudinal axis" 116 is intended to refer to the central axis of the container taken along the axis of elongation of the container. As shown in FIG. 1, the longitudinal axis 116 is a central axis extending between the base of the container (e.g., where the container is anchored or placed on the ground) and the opposing top end of the container. For simplicity, the exemplary systems and methods are described under the assumption that the base of the cylindrical container is anchored on flat ground and the circumferential wall of the container extends away from the ground in the longitudinal direction (i.e., in the vertical direction relative to the ground/base of the container). Accordingly, the directions that the longitudinal axis 116 extends is also referred to as the "longitudinal direction" 116. As can be appreciated, given a container assumed to be anchored to the ground at its base, and as you move away from the base, along the longitudinal axis, there is an infinite set of transverse or "latitudinal" planes extending through the cross-section of the container, on which the acoustic devices can be placed against the exterior surface of the container wall.

Two acoustic devices are described herein as being aligned in the longitudinal direction (also referred to as being in longitudinal alignment) when they have respective positions on the surface of the container that fall in the same transverse or latitudinal plane, which is a plane that is perpendicular to the longitudinal axis 116 and bisects the container 150. In other words, devices that are aligned in the longitudinal direction have the same height (i.e., latitude) relative to the base of the container along the longitudinal axis (e.g., both devices are 9 feet off the ground as measured from the base in the longitudinal direction).

Because the cylindrical container is a three-dimensional structure having a circumference, the term "circumferential direction" 118 is intended to refer to the direction along the surface 155 that extends about the circumference of the container and that is perpendicular to the longitudinal axis 116, at a given latitude. In particular, the circumferential direction about the container's circumference includes the counter-clockwise direction 114 and the clockwise direction 112, when viewing the container from above, for example.

Devices are referred to herein as being aligned in the circumferential direction, in circumferential alignment or circumferentially aligned, when their respective positions on the surface 155 fall in the same longitudinal plane (i.e. a plane extending through and along the longitudinal axis) and, preferably, the devices are on opposite sides of the container. For instance, two devices located at +270 degrees and +90, respectively, relative to a 0 degree reference axis 102 (when the cylindrical container is viewed from the top-view) are circumferentially aligned irrespective of their respective latitudes on the surface.

Because the surface of a wall of the container can also be described as an "unwrapped" two-dimensional surface, in two dimensional space, the circumferential direction 118 can be referred to as the "horizontal direction" (i.e., perpendicular to the longitudinal direction assuming that the base of the container is on level ground) or, more generally, the "transverse direction," which refers to one or more directions along the surface 155 that are perpendicular to the longitudinal direction 116, at respective latitudes.

Returning to FIG. 1, preferably, each transducer generates acoustic signals that travel from a respective point of origin through the interior volume 165 of the container 150. The terminology traveling "through the container" is intended to mean that the acoustic signal propagates through the thickness of the wall and across the interior volume 165 and, thus, through one or more mediums within the interior volume that lie in the signal's flightpath. In the exemplary system 100 deployed on the cylindrical storage container 150, the acoustic signals preferably travel through the cross-section of the container. However, it can be appreciated that, in some implementations, one or more of the transducers can be configured to generate acoustic signals that radiate along the surface 155 of the wall (e.g., propagate within the thickness of the wall) in one or more of the directions that the wall extends, for instance, in the circumferential direction 118, in the longitudinal direction 116, and/or a combination of the foregoing. Exemplary systems and methods for measuring container volume based on circumferentially traveling acoustic signals is more fully described in co-pending and commonly assigned U.S. Patent Application entitled "ACOUSTIC CALIBRATION ARRAY FOR TANKS AND VESSELS," to inventors Parrott et al., filed on [even date herewith], and bearing Ser. No. 15/491,588, which is hereby incorporated by reference as if fully set forth herein in its entirety.

As previously noted, in some configurations, the one or more transducers and one or more sensors are individual devices configured to operate in a "pitch-catch" mode, in which the transducers transmit the acoustic signals and they are received by the sensor. In addition or alternatively, at least a transducer and a sensor can be integrated into a single "transceiver" unit configured to both transmit and receive acoustic signals. In such an implementation, the transceiver can be configured to operate in "pulse-echo" mode, in which a transducer component transmits the pulse through the wall of the container and the interior volume towards an opposing sidewall of the container, and a sensor component receives the echo of the signal that is reflected off of the opposing wall of the container back toward the transceiver.

As shown in FIG. 1, the acoustic devices are electrically connected to (connection means not shown) a control computer 110 that is configured to coordinate the operation of the ultrasonic container volume calibration system 100 and the various acoustic devices. The control computer 110 is a computing device and/or data processing apparatus capable of communicating with the various devices of system 100, receiving, transmitting and storing electronic information and processing such information so as to measure and calibrate the volume of storage containers, as further described herein. As further described in relation to FIG. 2, the control computer comprises a processor (not shown), which executes one or more software modules in the form of machine implementable code and, in doing so, is configured to control the transmission and reception of ultrasonic signals by the transducer and sensors, respectively. In addition, the software configures the control computer to analyze the acoustic signal information, as generated by a transducer and measured by a sensor, and calculate various dimensions of the container (i.e., the container's geometry). In some implementations, the software can also configure the processor to evaluate structural conditions of the container as well as other operational characteristics of the container (e.g., the volume of the contents within the container, classify the contents, or structural integrity of the container walls, and the like).

More specifically, the control computer 110 is configured to determine the time between the generation of one or more acoustic signals by one or more transducers, such as transducer 130A, and the arrival of the one or more acoustic signals traveling through the wall and across the internal volume of the container at one or more of the sensors, such as, sensor 120A. Accordingly, the control computer is further configured to calculate the distance traveled by the signals and the dimensions of the container based on the time between the sound impulse and reception of the impulse waves and further based on a known speed of sound through the material of the wall. In addition, similar "time-of-flight" information for additional acoustic signals that arrive at the sensor(s) can be measured/collected using the control computer 110 as well, for instance, a time-of-flight for a reflection of a first acoustic signal, or the TOF of other acoustic signals generated by another transducer and the like.

As the speed of sound through the volume of the container can vary depending on the material properties of one or more mediums that the acoustic signals pass through, an accurate understanding of the speed-of-sound in the particular medium(s) contained within the container (i.e. oil, refined product, water, a mixture of mediums, and the like) is important to accurately determine the distance traveled by the acoustic signals and the dimensions of the container. More specifically, different liquids within the container will have different acoustic impedances, where this will relate to a different flight time. Also the presence of a different liquid may also be noted from the amplitude of the acoustic signal.

In some implementations, the speed of sound can be assumed based on the known contents of the container as well as known material properties of the container wall. For instance, the speed-of-sound in a known medium can be determined by performing offline measurement in a calibrated tank of known dimensions. In addition or alternatively, in some implementations, the system 100 can be configured to measure the speed of sound dynamically while the container is "online." More specifically, two (2) or more acoustic devices having a known separation can be used to calibrate the speed-of-sound measurement that informs the calibration of the container volume. For instance, the speed-of-sound calibration measurements can be carried out online by placing a base "strap" on the container having a known diameter, measuring the TOF of an acoustic signal transmitted across the diameter of the container and back-calculating the speed-of-sound based on the known diameter and measured TOF.

In some exemplary implementations, a single transducer and sensor can be utilized to conduct the container calibration, as further described herein. In some more complex implementations, one or more arrays of acoustic devices can be deployed onto the container and utilized to more accurately calculate the container dimensions. An array can comprise one or more acoustic sensors and, in addition or alternatively, one or more acoustic transducers.

In some implementations, the acoustic devices defining an array can be spaced apart a known amount in one or more directions along the surface. For instance, a phased array of multiple transducers that are spaced apart in one or more of the longitudinal direction 116 can be used. As further described herein, utilizing at least two acoustic devices that have a known spacing can aid in the calibration of the system 100 and accuracy assurance when using the system 100 to calibrate the volume of the container. Similarly, in some implementations, the acoustic sensors can be individually arranged at known circumferential positions around the container. As a result, the accuracy and speed of calculations can be improved. Moreover, based on the controlled placement of at least three acoustic devices relative to one-another on the container wall, the acoustic signal information can be used by the control computer to accurately triangulate and validate the respective positions of the acoustic devices. Thus, the dimensions of the container can be more accurately measured in multiple dimensions and used to create a two-dimensional model by "unwrapping" the outer wall of the container and, in addition or alternatively, a three-dimensional model of the container volume.

Acoustic Sensors:

The acoustic sensors, e.g., sensors 120A-120C, can be any variety of acoustic sensors or transceivers that are suitable for being mounted to the external surface of the container, detecting and receiving acoustic signals from the wall of the container and processing such information, as would be understood by those in the art. Preferably, the acoustic sensors have tips in contact with the surface 155 that are of a suitable size to achieve the required accuracy in the measurement and, thus, minimize error in detection of the acoustic signal. Accordingly, the size of the tip can be defined as a function of the necessary accuracy of the system.

In some exemplary configurations, piezoelectric transducers (contact transducers) can be used. In addition, dual element transducers that can transmit and receive acoustic signals (i.e. two piezoelectric crystals in the one transducer housing) can be used as well. Preferably in this case, the resonant frequency of the acoustic transducer can be below 1 MHz. Lower frequency transducers can be used (i.e., in the 100's of KHz range) where the time of flights can be compared. The frequency of the transducer can be selected based on the understanding that, as a result of attenuation of the signal, the expected amplitude will decrease as the frequency increases.

Preferably, the acoustic sensors are in electronic communication with the control computer 110 such that the control computer can control operation of the sensors and such that the sensors can provide acoustic signal data to the control computer for further processing. More specifically, in operation, the acoustic signals received by a sensor are converted to electrical signals that can be further processed, either by the sensor or the control computer, to extract signal measurement information including the temporal and intensity properties of the received acoustic signals.

Acoustic Signal Generators:

The basic principle of operation of an ultrasonic/acoustic signal generating device is that it converts an electrical signal to an acoustic signal, as would be understood by those in the art. As noted above, an acoustic signal generating device, also referred to as a transducer (e.g., transducer 130A-130C), can be any variety of acoustic transducers or transceivers that are suitable for generating acoustic signals that travel through the wall of the container 150 and across the internal volume 165 of the container and for being detected using the one or more sensors.

In the following description, the term "acoustic" is to be construed broadly to include any acoustic signals, for example in a frequency range of 100 Hz to 50 MHz, more optionally in the ultrasonic acoustic radiation range. Various types of acoustic signals can be used for instance, impulses/ pulses, a stream of pulses wherein the pulses occur at a particular frequency and each pulse has a particular waveform and resonant frequency (which is the frequency of the signal within the pulse), waves having a particular frequency, amplitude, wavelength and the like. In an exemplary preferred implementation, the acoustic transducer can be configured to generate a train of acoustic pulses. As would be understood, controlled parameters of the individual pulses in the train can include the period (1/frequency), resonant frequency and pulse duration. Parameters relating to the train can include a pulse repetition period and a duty factor. In such an implementation, the time between pulses is not critical factor, however, the time between pulses can be calculated and controlled such that pulses do not overlap. For instance, in the exemplary application of measuring storage containers, and considering the time of flight, delays between pulses of between 50 ms and 1000 ms second are suitable, although this is not a critical parameter (e.g., when traveling over thirty (30) meters the sound pulse should perform the return journey in close to 42 milliseconds). The frequency of the pulses can be determined by the resonant frequency of the transmitter. As mentioned above, a resonant frequency of the acoustic transducer below 1 MHz, and more optionally in the range of 10's to 100's of KHz, can be suitable in view of the distance traveled in the exemplary storage container measurement applications described herein.

A transducer can be configured to apply ultrasonic acoustic signals to the wall of the container 150 such that the signal radiates away from the point of origin of the signal. Preferably, the transducer is configured to be positioned relative to the surface of the container (e.g., at an angle that is normal to the container wall) and direct the acoustic signal such that it travels in one or more defined directions from the point of origin across the interior volume 165 of the container. In some configurations, the acoustic signal is directed along a specific path across the tank and perpendicular to the surface of the contact area between the acoustic transducer on the surface of the container wall. In some configurations, the transducer is configured to controllably transmit the acoustic signal across the interior volume of the container along a path that is perpendicular to the longitudinal axis 116 and along the diameter of the container. In addition or alternatively, the transducer is configured to controllably transmit the acoustic signal across the interior volume of the container at a given angle. For instance, directionality of the acoustic signal can be controlled by controlling the angle of the transducer relative to the container surface. More specifically, when operating in a pitch and catch mode, the acoustic signal can be transmitted at a known angle provided that the position of the catching transducer can be calculated and positioned adequately. Angled transmission (e.g., not directly across the container diameter) would increase the acoustic path travelled by the signal and can allow for a more accurate measurement of changes in volume of the tank. Such a configuration can also require a lower frequency signal (e.g., 10's to 100's of KHz) depending on the path length and as a result of signal attenuation within the container. In addition, in applications where the surface of a container may not accessible (e.g., an insulated container) the use of a waveguide may be used to direct the acoustic signal into the container.

Preferably, an acoustic transducer is in electronic communication with the control computer 110 such that the control computer can control operation of the transducer. In some implementations, the transducer can be configured to introduce acoustic signals having certain properties, namely, specific frequencies or specific ranges of frequencies. The properties of the acoustic signals can be a function of the specific hardware configuration of the transducer and, in addition or alternatively, controlled using the control computer.

In the case of using more than one transducer, the transducers can be individually controlled to facilitate differentiation between their respective signals. For instance, the transducers can be operated as a phased array, wherein the acoustic signals sent out by each transducer is controlled in time using the control computer 110, thereby allowing for the differentiation between signals received by the one or more acoustic sensors. In addition or alternatively, transducers that are configured to emit differing frequencies for emission and reception can be utilized to facilitate the differentiation between signals based on signal frequency using the control computer 110. Other suitable signal characteristics can also be selected or modulated in the methods and systems herein, for instance, the amplitude and wavelength of the acoustic signals can be modulated or defined by the control computer.

Robotic Deployment:

In some implementations, one or more of the acoustic devices can be attached in a respective position on the exterior of the container so as to provide a long-term or permanent calibration system capable of measuring a particular container's volume periodically in an on-demand fashion. In addition or alternatively, in some implementations, one or more of the acoustic devices can be deployed on a temporary basis such that the devices can be used to calibrate the volume of different containers. It can also be appreciated that a combination of fixed and temporarily deployed acoustic devices can also be utilized.

Accordingly, in some configurations, the system can include one or more robotic carriers or "robots" that are configured to autonomously and semi-autonomously deploy one or more of the acoustic devices on the container being calibrated, thus eliminating the need for scaffolding when deploying the devices into position on the container wall. For instance, as shown in FIG. 1, the acoustic transducer 130C can be controllably deployed using a robot 160. Deployment of an acoustic device by a robot can include attaching the device to the container at respective locations. Accordingly, in some configurations, a robot can deploy multiple different acoustic devices. In other configurations, an acoustic device can be mounted to a robot such that deployment comprises moving the robot into position and which places the acoustic device in acoustic communication with the surface 155 of the container wall and which can thereafter move to another position, as necessary. In such an arrangement, the robot can reposition itself and optionally move the acoustic device into engagement with the container under programmatic control of code implemented by the system.

As would be understood by those in the art of robotics, each robot 160 is a mobile robotic device that includes a body and a motion system for moving the robot during operation. The robot can be powered by, for example, solar cells, batteries, or any other suitable power source. The robot can include functional hardware components specifically designed to facilitate performing operational tasks, for instance, sensors for detecting height, position, orientation of the robot, and the like. The robot hardware can also include on-board acoustic sensors and transducers used in the container volume calibration processes and, in addition or alternatively, components suitable for transporting and deploying acoustic devices configured to operate in a stand-alone fashion. The robot can include electronic circuitry within the body that includes a memory and/or computer readable storage medium which are configured to store information relating to the operation of the robot such as configuration settings and one or more control programs that facilitate the performance of the container volume calibration operations.

According to a salient aspect, in some embodiments, the system 100 can be configured to controllably deploy the acoustic devices into position before and/or during implementation of the container volume calibration process so as to accurately measure the container volume in an automated fashion. More specifically, a robot-based deployment solution can be implemented to automatically execute more complex container volume calibration procedures with a high degree of precision thereby improving the accuracy of the container calibration results by virtue capturing acoustic measurements for any number of different sensor and/or transducer placement schemes. For example, robots can be controlled by the control computer 110 to systematically move the sensor(s) and/or the transducer(s) into different positions on the container wall (e.g., various heights, circumferential positions, relative positions, absolute positions etc.) such that acoustic measurements can be taken for each arrangement of devices and the measurements can thereafter be analyzed individually and in combination to generate a detailed map of the container's shape and, more particularly, the container volume.

Figure 2:
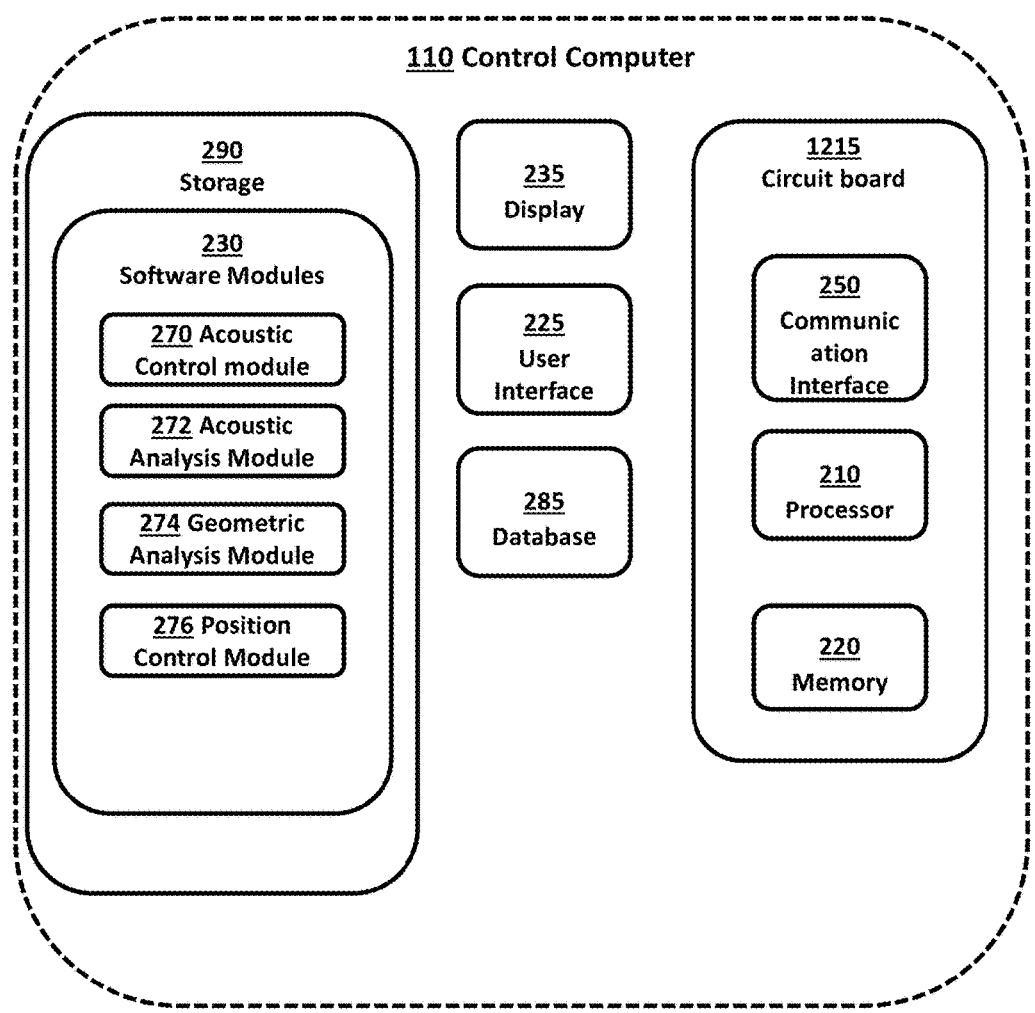
FIG. 2 is a block diagram illustrating an exemplary configuration of a control computer according to an embodiment of the present invention.

Control Computer:

The exemplary control computer 110 is further described in reference to FIG. 2. As shown, the control computer 110 can be arranged with various hardware and software components that serve to enable operation of the system 100, including a circuit board 215, a processor 210, a memory 220, a display 235, a user interface 225, a communication interface 250 and a computer readable storage medium 290.

The processor 210 serves to execute software instructions that can be stored in the storage 290 and loaded into the memory 220. The processor 210 can be a number of processors, a multi-processor core, or some other type of processor, depending on the particular implementation. The display can be displayed on a touchscreen or other display operatively coupled to an input device (not shown).

Preferably, the memory 220 and/or the storage 290 are accessible by the processor 210, thereby enabling the processor 210 to receive and execute instructions stored on the memory 220 and/or on the storage 290. The memory 220 can be, for example, a random access memory (RAM) or any other suitable volatile or non-volatile computer readable storage medium. In addition, the memory 220 can be fixed or removable. The storage 290 can take various forms, depending on the particular implementation. For example, the storage 290 can contain one or more components or devices such as a hard drive, a flash memory, a rewritable optical disk, a rewritable magnetic tape, or some combination of the above. The storage 290 also can be fixed or removable, local storage or remote storage such as cloud based data storage systems.

One or more software modules 230 are encoded in the storage 290 and/or in the memory 220. The software modules 230 can comprise one or more software programs or applications having computer program code, a script, or a set of interpretable instructions executed in the processor 210. Such computer program code or instructions for carrying out operations and implementing aspects of the systems and methods disclosed herein can be written in any combination of one or more programming languages or scripts. The program code can execute entirely on the control computer 110, as a stand-alone software package, partly on the control computer and partly on a remote computer/device (e.g., sensors, transducers and/or robots) or entirely on such remote computers/devices. In the latter scenario, the remote computer systems can be connected to control computer 110 through any type of electronic data connection or network, including a local area network (LAN) or a wide area network (WAN), or the connection can be made through an external computer (for example, through the Internet using an Internet Service Provider).

Preferably, included among the software modules 230 is an acoustic control module 270, an acoustic analysis module 272, a geometric analysis module 274, and a position control module 276 that are executed by processor 210. During execution of the software modules 230, the processor 210 is configured to perform various operations relating to the calibration of storage containers, as will be described in greater detail below.

It can also be said that the program code of the software modules 230 and one or more of the non-transitory computer readable storage devices (such as the memory 220 and/or the storage 290) form a computer program product that can be manufactured and/or distributed in accordance with the present disclosure, as is known to those of ordinary skill in the art.

It should be understood that in some illustrative embodiments, one or more of the software modules 230 can be downloaded over a network to the storage 290 from another device or system via communication interface 250 for use within the system for configuring field robots 100.

In addition, it should be noted that other information and/or data relevant to the operation of the present systems and methods can also be stored on the storage 290, for instance various control programs used in the operation of the acoustic devices (e.g., sensors and transducers) and/or the robots during use.

A database 285 can also be stored on the storage 290. Database 285 can contain and/or maintain various data items and elements that are utilized throughout the various operations of the system 100. The information stored in database 185 can include, but is not limited to, software and information for coordinating the operation of the acoustic devices, software and information for coordinating the movement of robots while deploying acoustic devices into their respective positions during container calibration, known characteristics used to perform the acoustic measurements and calculate container dimensions (e.g., container wall thickness, container wall material composition, container contents, container height, rough dimensions of the container). It should be noted that although database 285 is depicted as being configured locally to the storage of the control computer 110, in certain implementations, database 285 and/or various of the data elements stored therein can be located remotely and connected to the control computer 110 through a network in a manner known to those of ordinary skill in the art.

A communication interface 250 is also operatively connected to the processor 210 and can be any interface that enables communication between the control computer 110 and external devices, machines and/or elements such as the transducer, sensors and any robots used in connection with the calibration operations. Preferably, the communication interface 250 includes, but is not limited to, a modem, a Network Interface Card (NIC), an integrated network interface, a radio frequency transmitter/receiver (e.g., Bluetooth, cellular, NFC), a satellite communication transmitter/receiver, an infrared port, a USB connection, and/or any other such interfaces for connecting the control computer 110 to other computing devices and/or communication networks, such as private networks and the Internet. Such connections can include a wired connection or a wireless connection (e.g., using the IEEE 802.11 standard) though it should be understood that communication interface 250 can be practically any interface that enables communication to/from the control computer.

Figure 3:
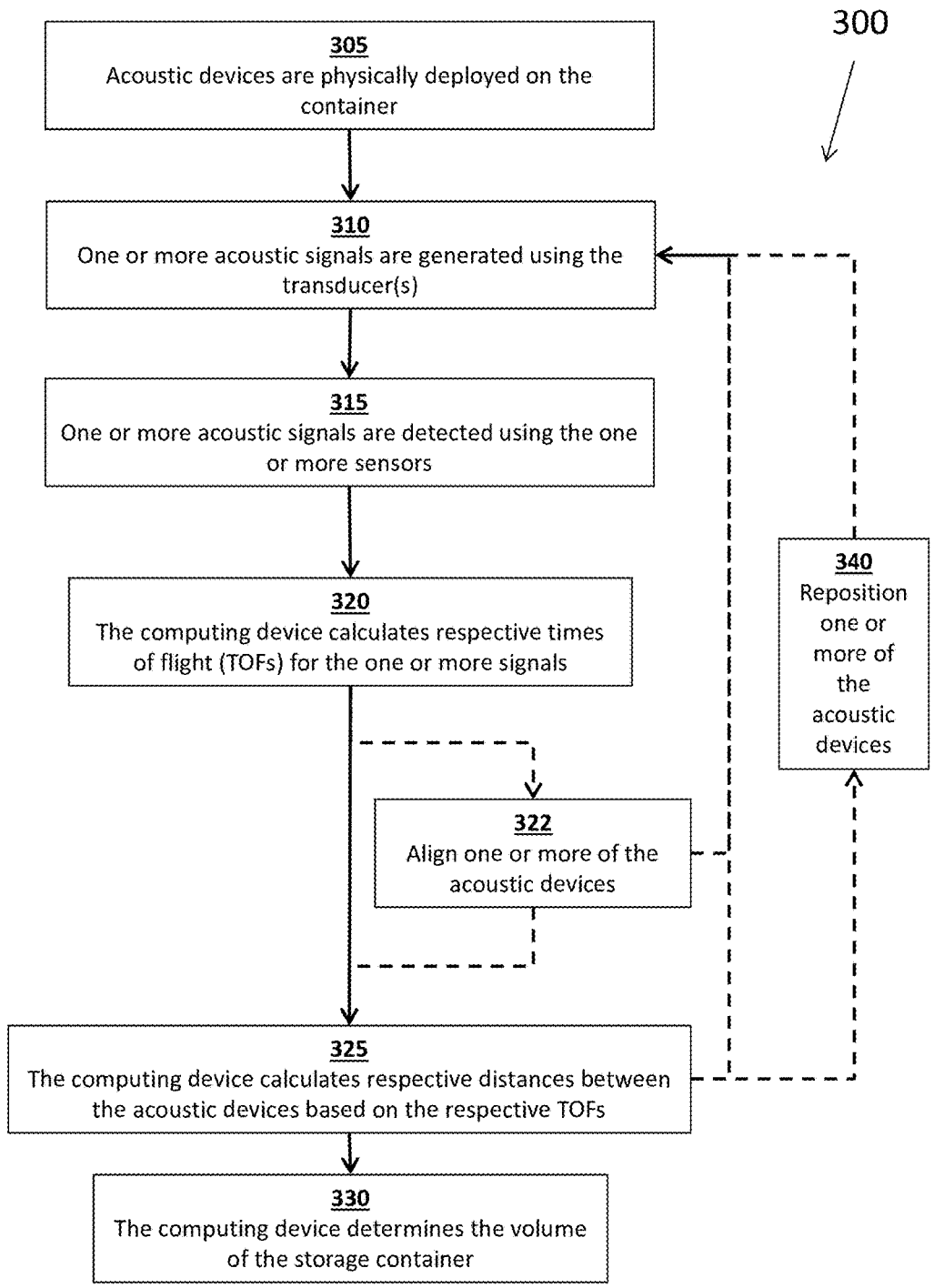
FIG. 3 is a flow diagram showing a routine that illustrates the systems and methods for ultrasonic calibration of the volume of storage containers according to an embodiment of the present invention.

Exemplary Methods of Operation:

The operation of the exemplary container volume calibration system 100 illustrated in FIG. 1 will be further appreciated with reference to FIG. 3. FIG. 3 is a high-level flow diagram of a routine 300 for calibrating the volume of a storage container according to one or more embodiments of the invention.

The routine 300 begins at step 305, when one or more acoustic devices are physically deployed on the container at respective positions. More specifically, one or more acoustic sensors and one or more acoustic transducers, such as, sensor 120A and transducer 130A, can be deployed into respective positions on the exterior surface 155 of the circumferential wall of the container 150 by hand or using a robot (e.g., 160) such that they are acoustically coupled to the surface and configured to transmit and/or receive acoustic signals that travel across the interior volume 165 of the container.

The respective "position" of an acoustic device should be understood as referring to the location (e.g., a point or area) on the surface of the container where the device transmits and/or receives the acoustic signals. Accordingly, in an implementation for calibrating the volume of the cylindrical storage container 150, the position of an acoustic device can include a particular latitude, as measured along the longitudinal axis 116, and a circumferential position measured in the circumferential direction 118. For instance, as shown in FIG. 1, transducer 130A has a height, h, relative to the container base 157, and is circumferentially positioned at a +270 degree angle about the container's circumference (measured relative to the 0 degree reference axis 102). It should be appreciated that alternative three-dimensional coordinate and positioning systems can be utilized without departing from the scope of the disclosed embodiments.

At step 310, one or more acoustic signals are generated using one or more of the deployed transducers. For instance, in the system 100 shown in FIG. 1A, the control computer 110, which is configured by executing one or more of the software modules including, for example and without limitation, the acoustic control module 270, can cause the transceiver 130A to generate an ultrasonic signal. The control computer can also record various parameters relating to the transmitted signals including, for example, an impulse time. Other recorded parameters can include the characteristics of the signal such as an intensity, frequency and the like. Preferably, the acoustic signal travels from the point of origin along a path extending across the interior volume 165 of the container 150, thereby traveling through the contained medium that is in the path of the acoustic signal.

At step 315, the one or more acoustic signals are detected using the one or more sensors. For instance, the acoustic signals emitted by transmitter 130A can be detected using the acoustic sensor 120A. In addition, at step 315, information relating to the detected acoustic signal(s) can be measured using the acoustic sensor and recorded by the control computer 110 for further processing. Preferably, this information includes a particular time that the arrival of the acoustic signal at the sensor is detected. In addition, the information measured and recorded for further analysis can include characteristics of the acoustic signal such as its intensity, frequency and the like. In some implementations, the characteristics of the one or more detected acoustic signals can be analyzed using the control computer to distinguish between different acoustic signals and, in some implementations, to determine various operational conditions of the container (e.g., the type of medium within the container at a given height, the container's structural condition, and the like), as further described herein.

Then at step 320, the control computer 110 calculates a time of flight (TOFs) for the one or more acoustic signals based on the impulse time and respective detection times for the one or more signals. Each respective TOF represents the elapsed time for a signal to travel between two of the acoustic devices and is a function of the distance traveled by the acoustic signal. More specifically, the control computer 110, which is configured by executing one or more of the software modules 130 including, for example and without limitation, the acoustic analysis module 272, can calculate a TOF for the one or more acoustic signals traveling along respective paths based on the elapsed time between the impulse time and respective times that the one or more signals were detected by the transceiver. For instance, the TOF of a signal transmitted by transducer 130A and received by sensor 120A is the time to travel along path, p, from the transducer's position to the sensor's position.

At step 325 the control computer 110 calculates the respective distance traveled by the one or more acoustic signals based on the measured TOFs and a speed of sound through the medium within the interior volume of the container. More specifically, the control computer 110, which is configured by executing one or more of the software modules 130 including, for example and without limitation, the geometric analysis module 274, can be configured to calculate the distance traveled by an acoustic signal along its respective paths as a function of the calculated TOF and the speed of sound through the medium. For instance, in an exemplary implementation where the transducer 130A and the sensor 120A are on opposite sides of the container 150, as shown in FIG. 1, and operating in a pitch-catch mode, with knowledge of the speed of sound in the medium, $v_{med}$, and the TOF measured for the acoustic signal travelling between the transducer and the sensor, the distance, d, can thus be calculated according to the equation ($d = 1/1 v_{med} \cdot TOF$).

At step 330, the control computer determines the dimensions of the storage container as a function of the one or more distances calculated at step 325 and a given alignment of the acoustic devices. More specifically, the control computer 110, which is configured by executing one or more of the software modules 130 including, for example and without limitation, the geometric analysis module 274, can be configured to calculate the diameter of the container 150 based on the acoustically measured distance traveled by the one or more acoustic signals and the known relative position of the acoustic devices that are used to measure the one or more distances. Similarly, given the measured diameter of the container, as measured from one or more positions on the container wall, the configured control computer 110 can also calculate the volume of the container based on known parameters of the container including its height.

In implementations where a transmitting transducer and a receiving sensor are independently positioned on the surface 155 of the container 150 and used to measure distance therebetween, the two devices are preferably aligned such that the acoustic signals transmitted therebetween travel along a path across the interior volume 165 that passes through the longitudinal central axis 116. In other words, the two devices are preferably located at diametrically opposed circumferential positions on the wall such that the signal travels across a diameter of the container. In addition, it can also be preferable for the two acoustic devices to be aligned in the longitudinal direction 116 (i.e., at the same latitude or height relative to the level base 157) such that the path traveled by the acoustic signals across the interior volume is also perpendicular to the longitudinal axis 116. Thus, where two acoustic devices are deployed at the same latitude and on opposite sides of the container wall, the distance, d, calculated at step 320 represents the diameter of the container at the given latitude.

Although the foregoing steps for calculating the diameter of the container are based on the assumption that independently deployed transducers and sensors are aligned in both the longitudinal and circumferential directions, TOF-based distance measurements between acoustic devices that are not so aligned can be similarly used to calculate the dimensions of the container, provided that the relative position of the two devices is known. For instance, as illustrated in FIG. 1, where acoustic transducer 130B and the acoustic sensor 120A are located at different latitudes, a projected diameter of the container 150 can still be calculated from an acoustically measured distance between the two devices, provided that the devices are circumferentially aligned on the outer surface 155 of the circumferential wall and the separation between the two devices in the longitudinal direction 116 (e.g., the difference between the heights of sensor 120A and transducer 130B, namely, h and h1, respectively) is known.

Because the positioning and alignment of the acoustic devices used to measure distance is important to achieving accurate measurements of the container, routine 300 can also include step 322 of aligning two or more acoustic devices. In accordance with one or more of the disclosed embodiments, the ultrasonic container volume calibration system 100 can be configured to automatically align two or more acoustic devices in one or more directions relative to the surface 155 of the circumferential wall of the container 150, for instance, the circumferential direction 118 and longitudinal direction 116. The alignment can be achieved and verified using acoustic-based distance measurements and, more specifically, based on the calculated TOFs of acoustic signals traveling between the devices being aligned.

In general, verifying that the devices are in alignment can include iteratively adjusting the position of one or more of the acoustic devices on the surface of the container in one or more directions and, for each position, repeating the steps of generating, detecting and re-calculating the TOF of acoustic signal(s) until the re-calculated TOFs indicate that the respective positions of the at least two of the acoustic devices are aligned. In some implementations, alignment can also include adjusting the angle of a transducer relative to the container, for instance, such that the acoustic signal travels across the interior volume along a path that is perpendicular to the longitudinal axis 116.

More specifically, by way of example and without limitation, the control computer 110, which is configured by executing one or more of the software modules 230, including, for example and without limitation, the position control module 276, can position and re-position the transducer 130C measured amounts in the longitudinal direction 116 along the surface 155 using the robot 160. Moving the transducer measured amounts in one or more directions on the container wall can be controlled based on position measurements gathered in near-real time, for instance, using one or more sensors that are on-board the robot that are suitable for measuring absolute position or relative position and movement of the robot (e.g., a GPS sensor, accelerometers, altitude sensors, and the like). For each new position of the robot and hence the transducer, the control computer can perform the steps of: generating one or more acoustic signals using the transducer, detecting the acoustic signals by the particular sensor that the transducer is being aligned with and calculating TOFs for the one or more signals. As noted, the control computer can be configured to cause the robot to separate the transducer or other acoustic device from the container, reposition the robot, then place the acoustic device back into engagement with the container at the new location. Preferably, when attempting to align the transducer 130C with a particular sensor, say, sensor 120B, TOF is calculated for the acoustic signals detected by the particular sensor 120B.

Because the TOF of soundwaves traveling between a transducer and a particular sensor are directly proportional to distance therebetween, alignment of the two devices in the longitudinal direction 116 can be achieved by iteratively moving the transducer (and/or the sensor) along the surface 155 in the longitudinal direction until a minimum value of TOF for a pulse traveling therebetween is identified. Similarly, alignment in the circumferential direction 118 can be achieved based on iteratively moving the transducer along the surface 155 (and/or the sensor) in the circumferential direction and re-measuring TOF until the TOF indicates that the devices are circumferentially aligned. For instance, assuming that the relative longitudinal position of transducer 130C and sensor 120B does not change, the two devices can be determined by the control computer to be circumferentially aligned (i.e., located at directly opposite circumferential positions) on the surface 155 of the wall when the TOF of acoustic signals traveling therebetween is at a maximum.

As previously noted, in some implementations, the calibration system 100 can be configured to measure the dimensions of the container 150 at different positions on the surface 155 in the longitudinal direction 116 and, in addition or alternatively, in the circumferential direction 118. Using distance measurements obtained in multiple dimensions, the control computer 110 can thus be configured to generate a model of the interior volume of the container with a greater degree of resolution and accuracy. Accordingly, the control computer 110 can be configured to repeat one or more of the steps of routine 300 (e.g., steps 305-325) for any number of different combinations of previously deployed sensors and transducers.

In addition or alternatively, at step 340, one or more of the acoustic devices can be re-positioned prior to re-measuring the distance between acoustic devices in view of the new position(s). For instance, the robot 160 can be configured to move acoustic transducer 130C from a first latitude to a second latitude such that the diameter of the container can be re-measured at the second latitude, and can thereafter move the transducer to another position, as necessary.

One or more steps of the exemplary routine 300 for measuring TOF and distance between acoustic devices using acoustic/ultrasonic measurement can be similarly implemented using various different transducer and sensor configurations and modes of operation. The remaining figures and corresponding discussion further illustrate various configurations and concepts of the ultrasonic container volume calibration system in accordance with one or more of the disclosed embodiments of the invention.

FIGS. 4A-9 illustrate exemplary container volume calibration systems having a variety of different acoustic device arrangements and modes of operation in accordance with one or more of the disclosed embodiments. It should be appreciated that the various acoustic devices illustrated in FIGS. 4A-4D are configured to be in communication with a control computer 110 (communication connection not shown) that coordinates operation of the acoustic container volume calibration system.

Figure 4A:
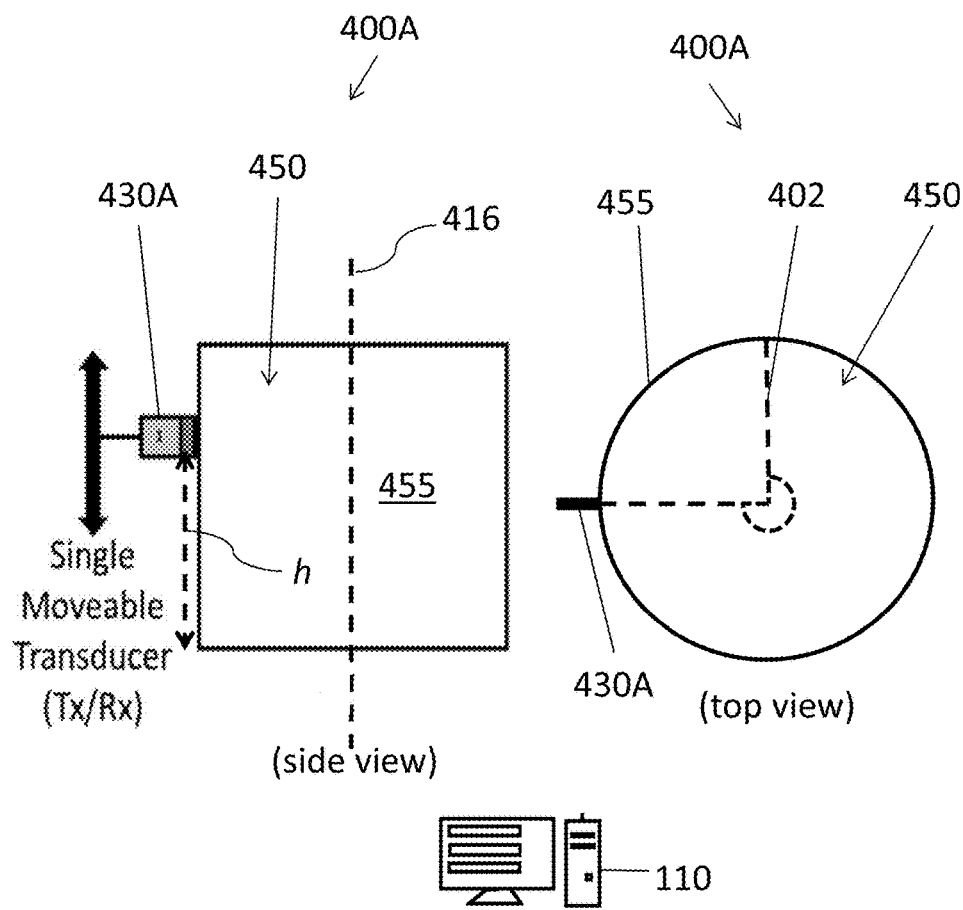
FIG. 4A is a simplified side view and top view of an exemplary container volume calibration system according to an embodiment of the present invention.

FIG. 4A is a high-level diagram showing a side-view and a top-plan view of an exemplary ultrasonic container volume calibration system 400A deployed on a container 450. The system 400A includes an ultrasonic transducer and sensor that are integrated into a singular transceiver unit 430A disposed on the exterior surface 455 of the circumferential wall of the container. In this exemplary configuration the transceiver can be configured to both transmit (Tx) and receive (Rx) acoustic signals (i.e., can operate in pulse-echo mode). As shown, the transceiver 430A is positioned at a height h on the wall, as measured in the longitudinal direction 416, and can be operated using the control computer 110 to measure the diameter of the container at height h.

Figure 4B:
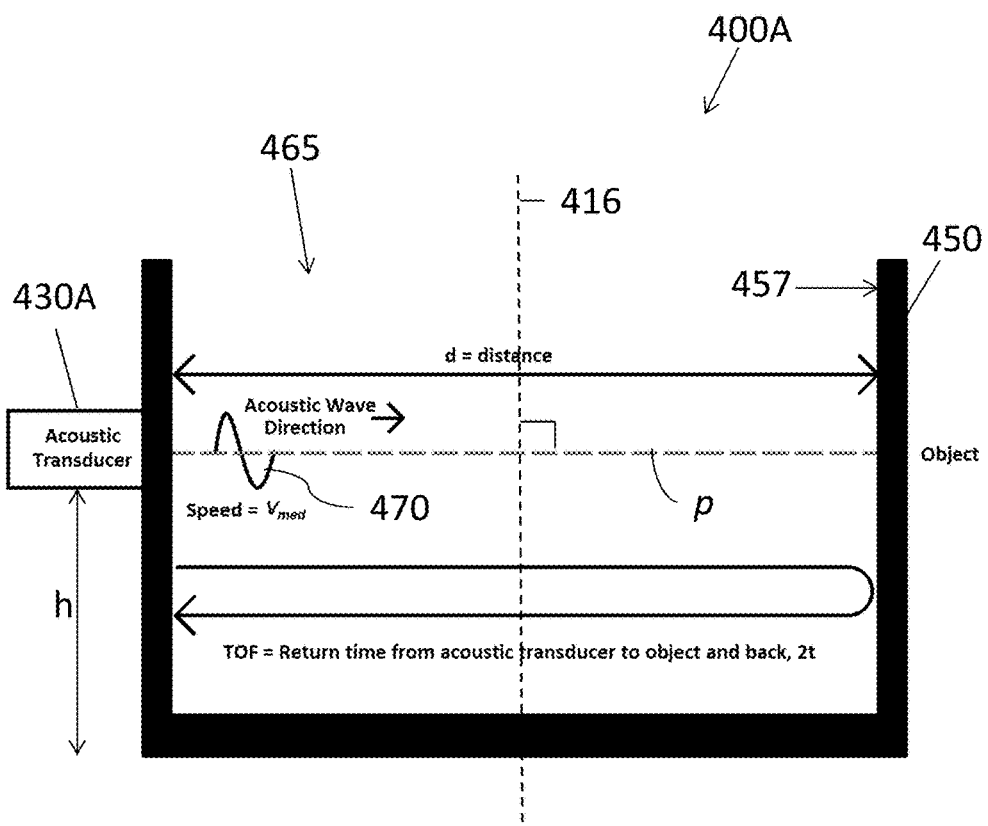
FIG. 4B, is a conceptual side-view of the exemplary container volume calibration system of FIG. 4A.

More specifically, the transceiver 430A can be configured to transmit an acoustic signal along a path across the interior volume of the container. The signal can be reflected by the interior surface of the circumferential wall on the opposite side of the container, such that at least a component of the reflected signal travels back along the path, p, toward the point of origin. Accordingly, the sensor component of the transceiver 430A, which is provided at effectively the same position as the transducer component, can be configured to detect the reflected acoustic signal and record the detection time and can also measure other characteristics of the received signal. FIG. 4B is a conceptual side-view diagram illustrating the travel of such an acoustic signal during operation of system 400A. As shown, the acoustic signal travels along the path, p, between the transceiver 430A and the interior surface 457 of the opposing side-wall. FIG. 4B also conceptually illustrates the TOF, which is the total "return time" for the acoustic signal to travel from the transceiver to the opposing wall and for a reflected component of the signal to travel back to the transceiver. FIG. 4B also illustrates the relationship between the distance between the transducer and the opposing wall, d, which is half the total distance traveled by the acoustic signal, 2d. Accordingly, with knowledge of the speed of sound in the medium, $v_{med}$, the distance between the transceiver and the opposing wall, d, can thus be calculated according to the equation ($d=\frac{1}{2}v_{med} \cdot TOF$).

Figure 4C:
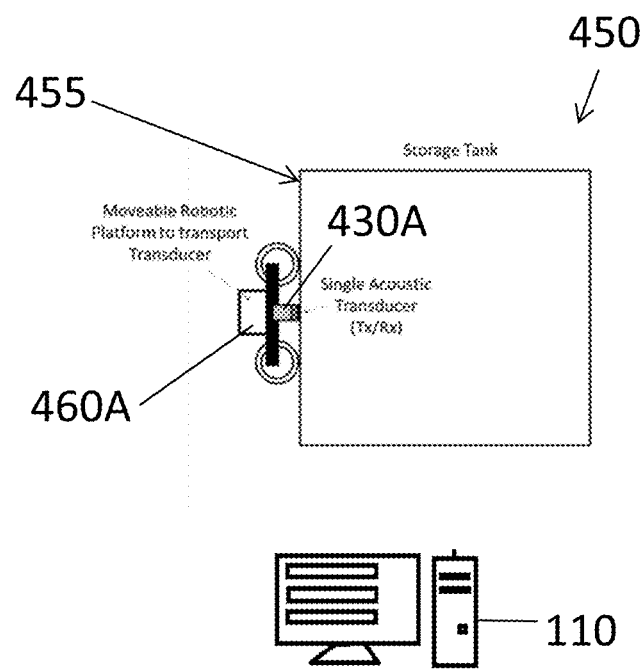
FIG. 4C is a simplified side view of the exemplary container volume calibration system of FIG. 4A.

In addition, the transceiver 430A can also be configured to be moved on the surface in one or more directions. For instance, as shown in FIG. 4C, the transceiver 430A can be mounted to a moveable robotic platform 460A, which is configured to autonomously or semi-autonomously move the transceiver into any number of different latitudes on the surface 455 of the container 450. Accordingly, the control computer 110 can controllably measure the diameter of the container at each respective latitude. In addition or alternatively, the transceiver 430A can be moved in other directions on the surface, namely, circumferentially, such that the container's diameter can be measured at multiple positions about the container's circumference, for instance, to determine the uniformity of the container's diameter at a given latitude.

Preferably, the acoustic transducer 430A operating in pulse echo mode is acoustically coupled to the surface 455 such that the acoustic signal travels to the inner surface of the opposing side of the container and is reflected back along the same path (e.g., a path that passes through the central longitudinal axis 416 of the cylindrical container and perpendicular thereto). Accordingly, positioning the transceiver can include the step of automatically aligning the transceiver relative to the surface 455 of the container so as to control the directionality of the acoustic signal transmitted. For instance, in some implementations, the robotic platform under the control of the control computer 110, can be configured to systematically adjust the angle of the transceiver 430A relative to the surface 455 until the acoustic signals is determined to travel along a path that passes perpendicularly through the longitudinal axis 416 (e.g., along a given latitude and normal to the opposing side of the container). The control computer can be configured to verify proper alignment based on one or more measured characteristics of the received acoustic signals (e.g., TOF, intensity, frequency and the like).

Figure 5:
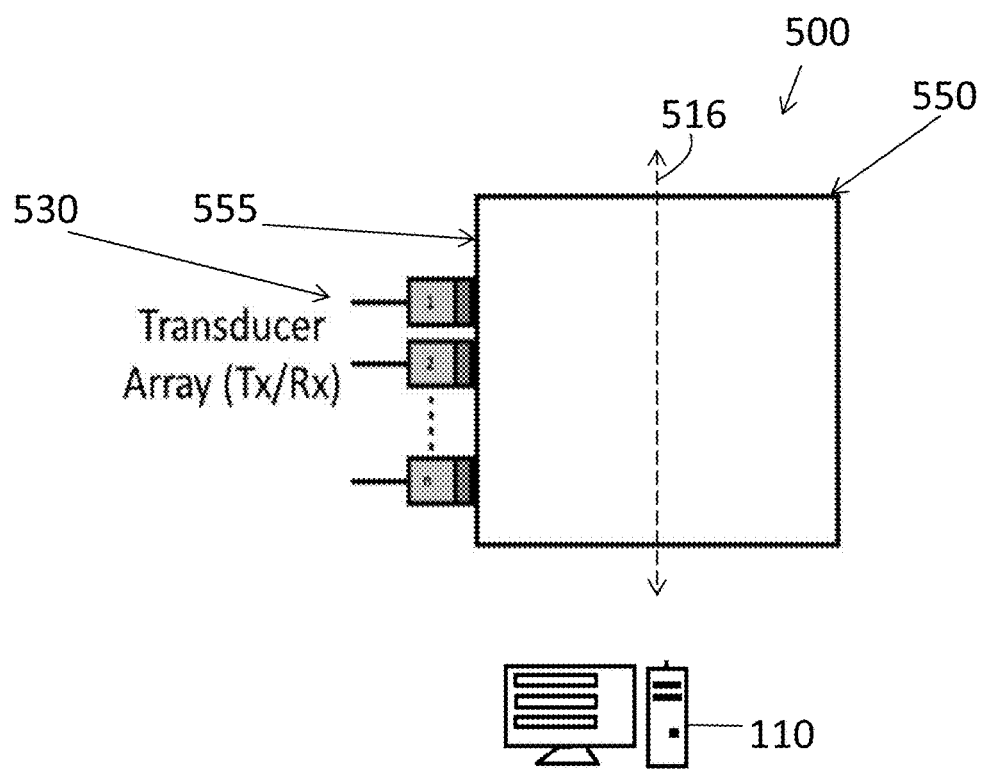
FIG. 5 is a simplified side view of an exemplary container volume calibration system according to an embodiment of the present invention.

In accordance with one or more of the disclosed embodiments, FIG. 5 illustrates another exemplary ultrasonic container volume calibration system 500 deployed on a container 550. The system 500 that includes an array 530 of transceiver units disposed on the exterior surface of a wall 555 of the cylindrical container. Like the transceivers described in connection with FIG. 4A, the individual transceivers 1-$n$ each comprise a transducer and sensor component and are configured to operate in both transmit (Tx) and receive (Rx) modes. As shown in FIG. 5, the transceivers can be provided at respective latitudes on the surface of the wall 455. In some implementations, the transceivers can be fixed at the respective positions. In addition or alternatively, one or more of the transceivers can be moveable in one or more directions on the surface.

It can be appreciated that, in accordance with the exemplary methods described in connection with FIGS. 1, 3 and 4A-4C, using the transducers 530A-N, individually, the control computer 110 can measure the diameter of the container 550 at the respective latitude of each transducer. As previously noted, in the case of systems using more than one transducer or transceiver, it can be preferable to use a phased array, wherein the acoustic pulses sent out by each element of the array is controlled in time, thus allowing for the differentiation between signals. In addition, or alternatively, another method that can be employed to differentiate the signals of respective transducers is for the transducers to operate at different respective frequencies for emission and reception. Although exemplary embodiments described herein measure distance between two devices operating as a pair, say, a first and a second transceiver, signals emitted by one device can be received by any number of other devices, i.e. a third transceiver, in a similar fashion to the "pitch and catch" between the first and second transceivers. In this way, the time of flight between the first and third transceivers will allow for calculation of the path distance there-between and thus calculation of the volume, provided that the relative positions of the devices is known (e.g., measured during device placement).

Figure 6:
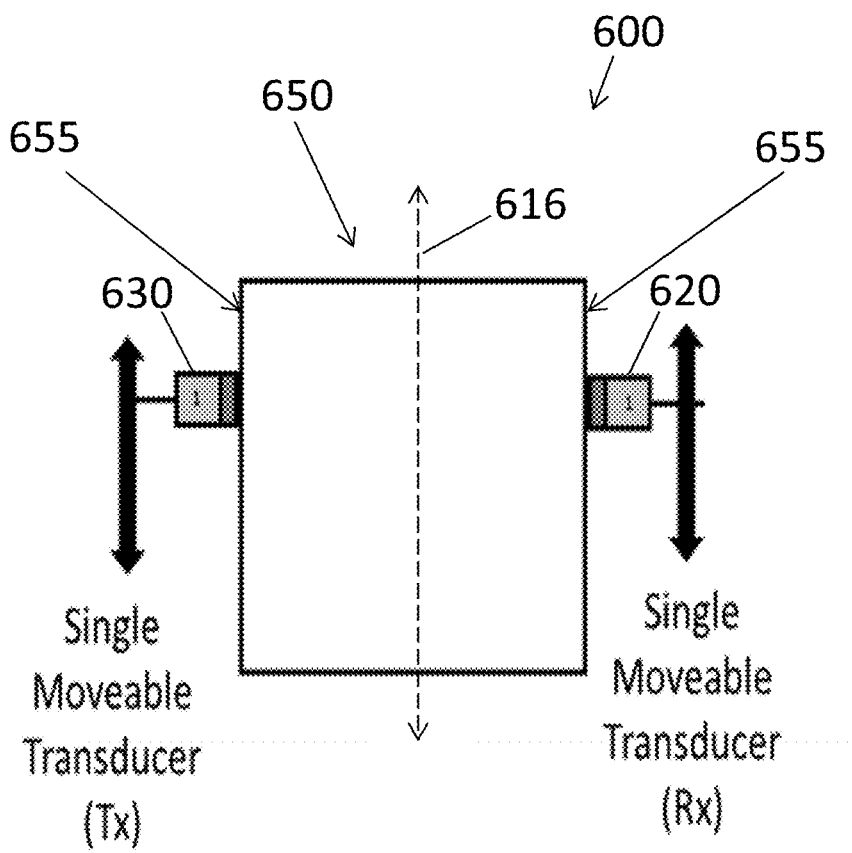
FIG. 6 is a simplified side view of an exemplary container volume calibration system according to an embodiment of the present invention.
Figure 6:
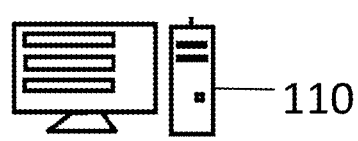

In accordance with one or more of the disclosed embodiments, FIG. 6 illustrates another exemplary ultrasonic container volume calibration system 600 deployed on a container 650. System 600 includes multiple acoustic devices including a transducer 630 and a sensor 620 disposed at respective positions on the exterior surface 655 of the circumferential wall of the cylindrical container. In such a configuration the transducer is configured to operate in transmit (Tx) mode, whereas the sensor is configured to operate in receive (Rx) mode. Accordingly, as described in connection with FIG. 3, the transducer and sensor pair can be configured to operate together in pitch-catch mode, namely, transmitting acoustic signals directly between the transducer and the sensor such that TOF along the direct flight-path can be measured and distance therebetween can be calculated. In addition, the transceiver 430C and sensor 420 can also be configured to be moved in the longitudinal direction 616, for instance, to enable the measurement of the container's diameter at different latitudes. In addition or alternatively, the transducer and sensor can also be moved in other directions on the surface, namely, the circumferential direction, so as to measure diameter at multiple positions about the circumference of the container.

Figure 7:
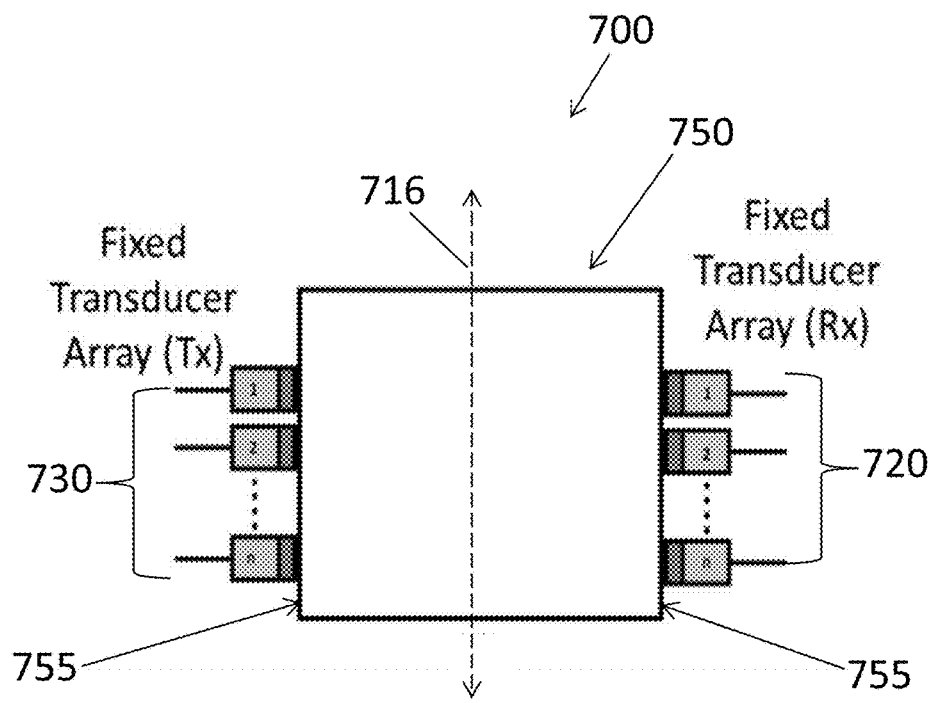
FIG. 7 is a simplified side view of an exemplary container volume calibration system according to an embodiment of the present invention.
Figure 7:

In accordance with one or more of the disclosed embodiments, FIG. 7 illustrates another exemplary ultrasonic container volume calibration system 700 deployed on a cylindrical container 750. System 700 includes an array 730 of transducer devices 730-1 to 730-n and an array 720 of sensor devices 720-1 to 720-n disposed on the exterior surface 755 of a circumferential wall of the container. In such a configuration each transducer can be configured to operate in transmit (Tx) mode, whereas each sensor can be configured to operate in receive (Rx) mode such that one or more of the transducers in array 730 and one or more of the sensors in array 720 can be configured to operate together in pitch-catch mode. As shown, the transducers and sensors can be provided at opposing circumferential positions. The devices can also be provided at respective latitudes and the respective positions can be fixed. Preferably, each one of the transducers is positioned at the same latitude as one of the sensors thereby defining respective pairs, for instance, transducer 730-1 and corresponding sensor 730-1 define a pair at a given height. However, in some implementations, individual transducers and sensors are not necessarily paired-up in a one-to-one fashion or at the same latitude as another device. In addition or alternatively, in some implementations, one or more of the acoustic devices can be moveable in one or more directions along the surface of the wall.

Figure 8:
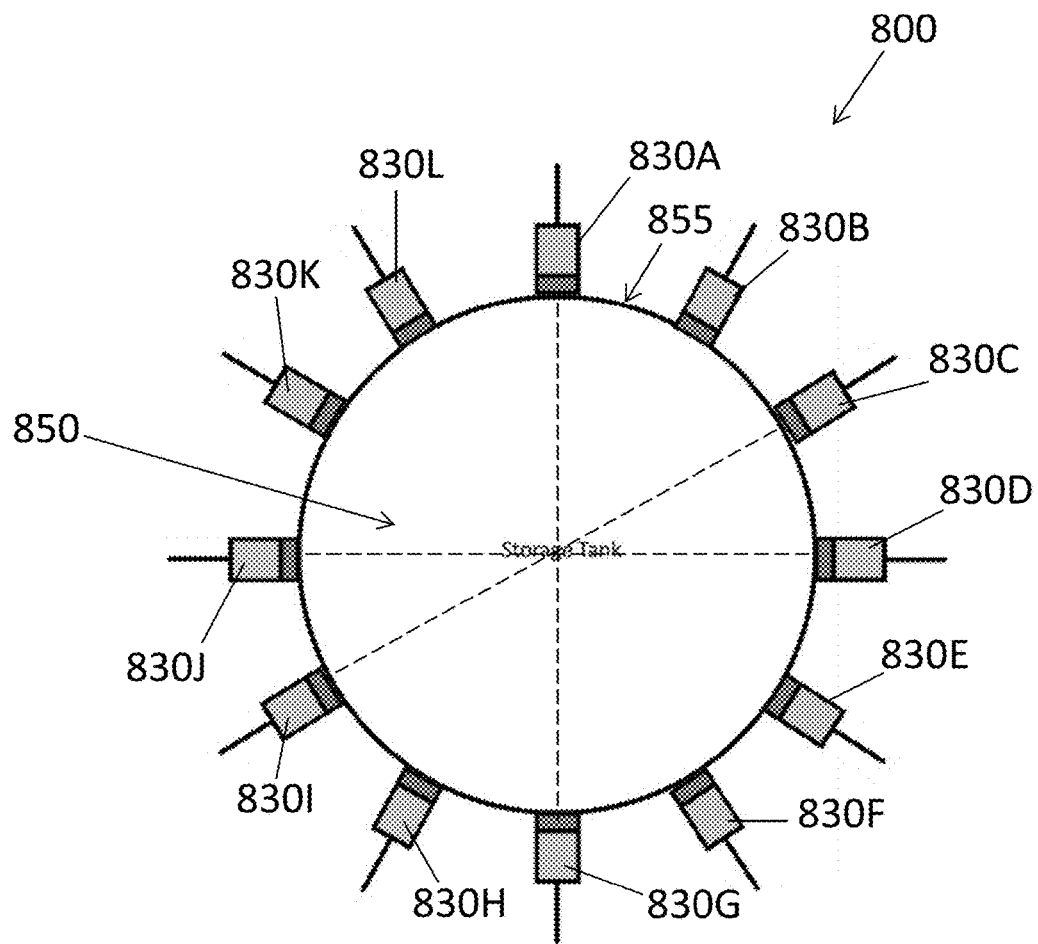
FIG. 8 is a simplified top view of an exemplary container volume calibration system according to an embodiment of the present invention.
Figure 8:
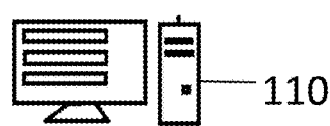
Figure 9:
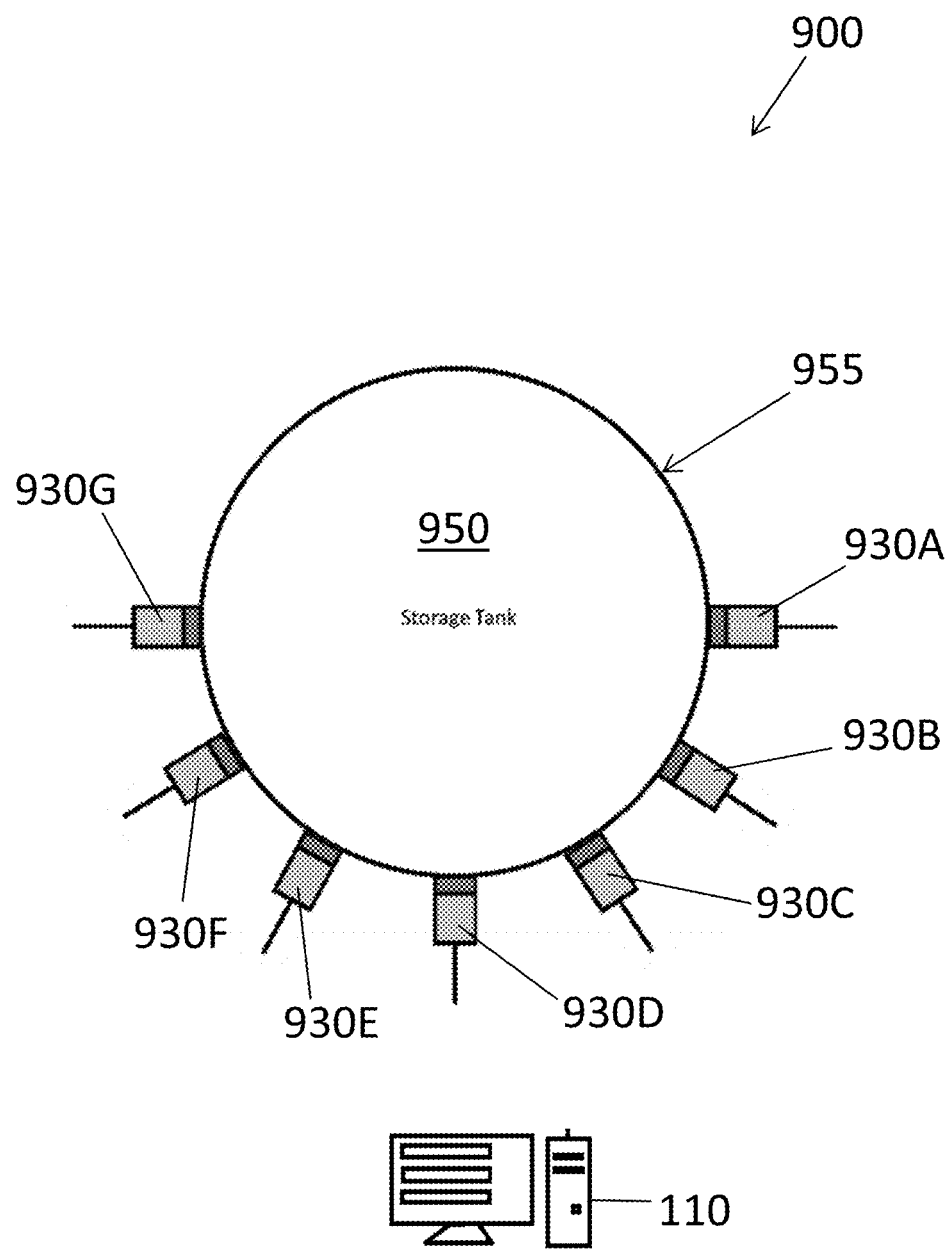
FIG. 9 is a simplified top view of an exemplary container volume calibration system according to an embodiment of the present invention.

FIG. 8 is a top view of an exemplary ultrasonic container volume calibration system 800 deployed on a container 850, in accordance with one or more of the disclosed embodiments. As shown, system 800 includes an array 830 of acoustic devices 830A-830L disposed circumferentially about the exterior surface 855 of a circumferential wall of the cylindrical container. As shown, the devices are spaced about the complete circumference of the container. In the exemplary system 800, devices that are at opposing circumferential positions on the cylindrical container, e.g., transducer/transceiver 830A and sensor/transceiver 830G, can operate in transmit and receive modes, respectively. By way of further example, FIG. 9 is a top view of an exemplary ultrasonic container volume calibration system 900 deployed on a circumferential side-wall 955 of a container 950. As shown in FIG. 9, the system 900 includes acoustic devices spaced 930A-930G about a part of the circumference of the container, for instance, half of the circumference of the container. As the acoustic devices are only spaced about part of the circumference, preferably, transceivers operating in both transmit and receive modes are used.

In the exemplary implementation shown in FIG. 8, the location of the transducers about the circumference of the container can be operated using the control computer 110 to provide a cross-sectional image of the tank and its contents. For instance, known mathematical algorithms can be used to generate the image such as back projection algorithm (i.e. radon transfer) and other such algorithms. In implementations such as illustrated in FIG. 9 where the acoustic devices provide partial coverage of the container's circumference, the control computer can still be configured to generate a cross sectional image of the container using similar mathematical techniques. It should also be noted that the number of transducers used is directly proportional to the resolution of the image of the container volume that can be generated using the control computer.

It should be understood that a combination of the configurations and modes of operation described in connection with FIGS. 5A-9 can be utilized to acoustically calibrate the volume of containers in accordance with one or more of the disclosed embodiments. For example, the container volume measurements taken utilizing fixed arrays of acoustic devices can be supplemented by measurements taken using robot-mounted acoustic devices configured to measure container dimensions at locations that are not otherwise monitored by the fixed devices and otherwise hard to reach locations on the wall of the container. By way of further example, although FIGS. 8 and 9 depict only a single acoustic device placed at respective circumferential positions, in some implementations, a longitudinally oriented array of devices can be deployed at one or more of the respective circumferential positions on the container wall, for instance, as described in connection with FIGS. 5 and 7. In implementations where arrays comprise transducers (or transceivers) arranged in the longitudinal direction (e.g., spaced apart on the surface of the wall in a vertical line relative to the base) and where several such arrays are placed around the circumference of the tank, the use of multiple arrays can allow measurement of the tank at different points in the longitudinal and circumferential direction. The resolution of the container volume models or images generated by the control computer 110 can depend on the number of devices in each array as well as the number of arrays deployed onto the wall of the container. Accordingly, with a sufficient number of longitudinal arrays located around the circumference of the tank the control computer can generate a sufficiently detailed two-dimensional or three-dimensional images of the container volume and its contents.

As noted, in addition to measuring the volume of a container, the exemplary systems and methods for acoustically calibrating the volume of storage containers can also be configured to acoustically determine operational characteristics of the container including, the type of contents within the container, the volume of such contents and evaluate the structural integrity of the container walls.

More specifically, the acoustic measurements can be used to measure the level of liquid(s) within the tank thereby allowing a calculation of the liquid volume. For instance, when utilizing an array of acoustic devices spaced apart to measure the diameter of the tank at respective latitudes, the control computer can be configured to analyze the characteristics of the signals measured at respective latitudes to identify a level of an interface between two different mediums, say, an interface between petroleum and air. Accordingly, the volume of petroleum within the container can be determined based on the interface level and the volume of the portion of the container that extends between the base and the interface level, or, by way of further example, the height difference between the oil/air interface and an oil/water interface closer to the base).

By way of further example, as a result of the different speeds of sound in media (e.g., in this particular application hydrocarbon, air and water) the calibrated system can differentiate between each media. For instance, in the case of air, there typically will be no signal due to high signal attenuation at the operating frequency of the transducers.

Accordingly, the system can determine the interface between oil and air at the point where no signal is received.

In addition, with knowledge of the speed of sound of the acoustic signals in the medium, the system can be further configured to classify the specific type of product contained within the storage container. More specifically, as would be understood by those in the art, the speed of sound in air (330 m/s) is quite different from the speed of sound in the media contained with the storage vessel. The speed of sound in water is close to 1484 m/s, and the speed of sound through kerosene is close to 1324 m/s. As a practical example, transmitting an acoustic signal over a distance of 30 meters would equate to a time of flight (return journey) of 40.43 seconds for water and 45.31 seconds for kerosene. Accordingly, with calibration of the container dimensions or expected times of flight, the system can be configured to determine the liquid in the tank at a given level measured with a transducer according to the difference in time of flight.

Moreover, the foregoing concepts can also be used to identify the presence of other liquids, e.g., water at the bottom of the petroleum storage container. Such information can be used to ensure an accurate determination of the volume of container contents and thus ensure the correct transfer of product to and from the container and potentially avoid contamination of other tanks/vessels.

As noted, the system can also be configured to evaluate the structural integrity of the container walls, preferably. The system can be configured to measure container integrity independent of or in connection with the processes for measuring container volume. More specifically, the system can be configured to transmit an acoustic signal using a transceiver (operating in Tx and Rx mode) and, when the acoustic signal is initially sent by a transceiver, part of the signal will be reflected off the boundaries of the container wall, while part of it will transmit through the internal volume as described above. The signal that reflects off the boundary (i.e., internal surface of the container wall) will represent information on the thickness of the vessel and can be received and measured using the transducer. In particular, based on a known speed of sound in the wall material and the time of flight (return trip to boundary wall) the system can calculate the thickness of the wall. In addition or alternatively, a high frequency transducer can be used to measure the integrity of the internal structure of the boundary walls of the container, e.g., cracking and blistering, based on the measured return time of flight and speed of sound in the material. Accordingly, in another exemplary configuration, the system can incorporate a dual frequency transducer, wherein signals emitted at a high frequency can be analyzed to measure vessel integrity and lower frequency signals can be analyzed to perform the time of flight measurement of container dimensions. In addition, in such dual-frequency transceiver configurations, electronic filtering techniques can also be applied to remove noise, as necessary (e.g., using a Low and/or High Pass filter).

At this juncture, it should be noted that although much of the foregoing description has been directed to systems and methods for ultrasonic calibration of the volume of storage containers, the systems and methods disclosed herein can be similarly deployed and/or implemented in scenarios, situations, and settings far beyond the referenced scenarios. For instance, the exemplary systems and methods can be adapted to acoustically measure the volume of containers without limitation to ultrasonic acoustic devices.

Although the exemplary systems and methods for measuring container volume based on acoustics are described above in the context of a particular practical application, namely, measuring the volume of large petroleum storage containers having a cylindrical shape and metallic construction, it should be understood that the disclosed embodiments of the invention are not limited to this exemplary application. For instance, the disclosed systems and methods can be used to measure the volume of storage containers having alternative shapes (e.g., spherical containers, cube-shaped containers and the like). For example and without limitation, in the case of a cube shaped container, the methods disclosed above can be similarly applied to align acoustic devices on the exterior surface of the container along a longitudinal axis and/or transverse axis, acoustically measure the distance between opposing walls of the container at multiple heights and multiple positions about the periphery of the container and, accordingly, generate two or three dimensional maps of the interior volume of the container, its contents and the like.

It should be appreciated that more or fewer operations can be performed than shown in the figures and described. These operations can also be performed in a different order than those described. It is to be understood that like numerals in the drawings represent like elements through the several figures, and that not all components and/or steps described and illustrated with reference to the figures are required for all embodiments or arrangements.

Thus, illustrative embodiments and arrangements of the present systems and methods provide a system and a computer implemented method, computer system, and computer program product for ultrasonic calibration of the volume of storage containers. The flowchart and block diagrams in the figures illustrate the architecture, functionality, and operation of possible implementations of systems, methods and computer program products according to various embodiments and arrangements. In this regard, each block in the flowchart or block diagrams can represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising", when used in this specification, specify the presence of stated features, integers, steps, operations, elements, and/or components, but do not preclude the presence or addition of one or more other features, integers, steps, operations, elements, components, and/or groups thereof.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

The subject matter described above is provided by way of illustration only and should not be construed as limiting. Various modifications and changes can be made to the subject matter described herein without following the example embodiments and applications illustrated and described, and without departing from the true spirit and scope of the present disclosure, which is set forth in the following claims.

What is claimed is:

1. A method of measuring an interior volume of a storage container containing a medium therein using a plurality of acoustic devices, the method comprising:
deploying, with a robot that includes a drive system and one or more position sensors for monitoring a position of the robot, the plurality of acoustic devices into respective positions on an exterior surface of a circumferential wall of the container, the acoustic devices including an ultrasonic transducer and an ultrasonic sensor, wherein the transducer is acoustically coupled to the surface and is configured to transmit one or more ultrasonic signals through the wall of the container and across the interior volume of the container, and wherein the sensor is acoustically coupled to the surface and configured to detect the one or more ultrasonic signals;
transmitting one or more ultrasonic signals using the transducer, wherein each signal is transmitted at a respective impulse time;
detecting, using the sensor, an arrival of the one or more signals and recording a respective detection time;
calculating, by a computing device in electronic communication with the transducer and the sensor, respective times of flight (TOFs) for the one or more signals travelling between the respective positions of the transducer and the sensor based on the respective impulse times and respective detection times, wherein a respective TOF is an elapsed time for a signal to travel along a path between the respective positions of the transducer and the sensor;
aligning, with the computing device based on the respective TOFs, the one or more of the transducer and the sensor in one or more of a circumferential direction and a longitudinal direction relative to the circumferential wall of the container, wherein the step of aligning comprises:
adjusting the respective position of one or more of the transducer and the sensor on the surface in one or more of the circumferential direction and the longitudinal direction,
for each adjusted respective position, performing the steps of transmitting, detecting and calculating respective TOFs based on one or more acoustic signals traveling therebetween, and
determining based on the calculated TOFs, whether the transducer and sensor are aligned in one or more of a circumferential direction and a longitudinal direction relative to the surface of the container;
calculating, with the computing device, a distance between the respective positions of the aligned transducer and sensor based on the calculated respective TOF and a speed of sound through the medium; and
determining, with the computing device, the volume of the storage container based on the calculated distance and the respective positions of the aligned transducer and sensor.

2. The method of claim 1, repeating the adjusting, transmitting, detecting and calculating steps until determining, with the computing device based on the calculated TOFs, that the transducer and the sensor are aligned.

3. The method of claim 2, wherein the step of adjusting the respective position of one or more of the transducer and the sensor on the surface comprises:
moving one or more of the transducer and the sensor a prescribed amount in one or more of the longitudinal and the circumferential direction using a robot operating under the control of the computing device, wherein the prescribed amount is measured in near-real time using one or more position sensors on-board the robot and wherein the robot is configured to move according to a feedback control loop.

4. The method of claim 1, further comprising:
deploying a plurality of sensors at different respective positions on the surface;
iteratively aligning, using a robot under the control of the computing device, the transducer with each one of the plurality of sensors;
performing the steps of generating, detecting and calculating respective TOFs for each respective position of the transducer that is aligned with one of the plurality of sensors; and
calculating, based on the calculated TOFs, a diameter of the container for each respective position of the transducer that is aligned with one of the plurality of sensors.

5. The method of claim 1, further comprising:
adjusting the respective position of one or more of the transducer and the sensor on the surface in one or more of the circumferential direction and the longitudinal direction using one or more robots under the control of the computing device, and
performing the steps of transmitting, detecting and calculating respective TOFs for one or more acoustic signals transmitted between the adjusted respective positions of the transducer and sensor.

6. The method of claim 1, further comprising:
prior to the step of calculating the distance, measuring the speed of sound in the medium.

7. The method of claim 6, wherein the step of measuring the speed of sound in the medium comprises:
deploying a particular transducer and a particular sensor at respective positions on the surface having a known distance therebetween;
measuring, with the computing device using the particular transducer and sensor, TOF for at least one acoustic signal transmitted between the particular transducer and the particular sensor; and
calculating, with the computing device, the speed of sound through the medium based on the TOF of the signal traveling between the transducer and the particular sensor and the known distance.

8. The method of claim 1, further comprising:
identifying, with the computing device based on the calculated respective TOFs, one or more of: a type of a medium contained within the storage container, a volume of the medium contained within the storage container.

9. The method of claim 1, wherein the transducer and the sensor are combined into an acoustic transceiver unit that is configured to both transmit and receive the one or more ultrasonic signals, and wherein the step of aligning comprises:
controllably positioning the transceiver relative to the circumferential wall of the container such that the one or more acoustic signals travel along a path extending across the internal volume of the container along a diameter of the container.

10. A system for measuring a volume of a storage container, the system comprising:
a plurality of acoustic devices configured to be acoustically coupled to an exterior surface of a circumferential wall of the container at respective positions, the acoustic devices including:
an ultrasonic transducer configured to transmit one or more ultrasonic signals across an interior volume of the container that is bounded by the wall, and
an ultrasonic sensor configured to detect the one or more ultrasonic signals;
a robot configured to controllably deploy one or more of the acoustic devices on the surface, wherein the robot includes a drive system and one or more position sensors for monitoring a position of the robot; and
a control computing system comprising:
a non-transitory computer readable storage medium,
one or more processors in electronic communication with the plurality of acoustic devices, the robot and the computer readable storage medium,
one or more software modules comprising executable instructions stored in the storage medium, wherein the one or more software modules are executable by the processor and include:
an acoustic control module that configures the processor to, using the transducer, transmit one or more acoustic signals at respective impulse times, wherein the acoustic control module further configures the processor to, using the sensor, detect the arrival of the one or more signals and record respective detection times,
an acoustic analysis module that configures the processor to calculate a respective time of flight (TOF) for the one or more acoustic signals traveling between the respective positions of the transducer and the sensor, and calculate a respective distance therebetween based on the respective TOF,
a position control module that configures the processor to, using the robot, adjust the respective position of one or more of the transducer and the sensor on the surface and, for each adjusted respective position, re-calculate a respective distance between the transducer and the sensor based on one or more acoustic signals traveling therebetween, and wherein the position control module configures the processor to determine based on the calculated TOFs, whether the transducer and sensor are aligned in one or more of a circumferential direction and a longitudinal direction relative to the surface of the container, and
a geometric analysis module that configures the processor to calculate a volume of the storage container based on the calculated respective distances and corresponding respective positions of the transducer and the sensor.

11. The system of claim 10, wherein the position control module configures the processor to iteratively adjust the respective position of one or more of the transducer and the sensor on the surface and re-calculate TOF until determining that the transducer and sensor are aligned.

12. The system of claim 10, further comprising: a plurality of ultrasonic sensors including at least a first acoustic sensor and a second acoustic sensor, wherein the plurality of sensors are separated by a known distance in one or more of the circumferential direction and the longitudinal direction.

13. The system of claim 10, wherein the position control module configures the processor to, using the robot, align the transducer with each of the plurality of sensors in the longitudinal direction and circumferential direction and, for each respective position in which the transducer is aligned with one of the plurality of sensors, calculate a respective diameter of the container based on the calculated TOFs.

* * * * *